United States Patent
Yao et al.

(10) Patent No.: US 9,782,400 B2
(45) Date of Patent: *Oct. 10, 2017

(54) ONCOGENIC ROS1 AND ALK KINASE INHIBITOR

(71) Applicant: Macau University of Science and Technology, Taipa, Macau (CN)

(72) Inventors: Xiao Jun Yao, Taipa (CN); Lai Han Leung, Taipa (CN); Lian Xiang Luo, Taipa (CN); Liang Liu, Taipa (CN)

(73) Assignee: Macau University of Science and Technology (MO)

( * ) Notice: Subject to any disclaimer, the term of this patent is extended or adjusted under 35 U.S.C. 154(b) by 0 days.

This patent is subject to a terminal disclaimer.

(21) Appl. No.: 14/956,620

(22) Filed: Dec. 2, 2015

(65) Prior Publication Data

US 2016/0367547 A1    Dec. 22, 2016

Related U.S. Application Data

(63) Continuation-in-part of application No. 14/744,042, filed on Jun. 19, 2015, now Pat. No. 9,526,722.

(30) Foreign Application Priority Data

Jun. 24, 2015 (AU) ............................... 2015100840
Nov. 26, 2015 (AU) ............................... 2015101722

(51) Int. Cl.
    *A01N 43/42*      (2006.01)
    *A61K 31/444*     (2006.01)
    *A61K 31/4745*   (2006.01)

(52) U.S. Cl.
    CPC ............................. *A61K 31/4745* (2013.01)

(58) Field of Classification Search
    CPC .............. A61K 31/4745; C07D 495/14; C07D 513/04; C12N 2310/321; C12N 2310/346; C12N 2310/341
See application file for complete search history.

(56) References Cited

PUBLICATIONS

Lim et al, Plos One, Sep. 14, 2015.*
Mazieres et al. JCO, Feb. 2015.*
Rolfo et al, Transl Lung Cancer Res. Aug. 2014; 3(4): 250-261.*
Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*
Jemal, A. et al. Cancer statistics, 2009. CA: a cancer journal for clinicians 59, 225-249 (2009).
Shaw, A.T., Hsu, P.P., Awad, M.M. & Engelman, J.A. Tyrosine kinase gene rearrangements in epithelial malignancies. Nature reviews. Cancer13, 772-787 (2013).
Looyenga, B.D., Cherni, I., Mackeigan, J.P. & Weiss, G.J. Tailoring tyrosine kinase inhibitors to fit the lung cancer genome. Translational oncology4, 59-70 (2011).
Christine M. Lovly1 and William Pao1 Escaping ALK inhibition mechanisms of and strategies to overcome resistance. Science translational medicine4, 1-5 (2012).
Takeuchi, K. et al. RET, ROS1 and ALK fusions in lung cancer. Nature medicine18, 378-381 (2012).
Kwak, E.L. et al. Anaplastic lymphoma kinase inhibition in non-small-cell lung cancer. The New England journal of medicine363, 1693-1703 (2010).
Roskoski, R., Jr. Anaplastic lymphoma kinase (ALK): structure, oncogenic activation, and pharmacological inhibition. Pharmacological research68, 68-94 (2013).
Gandhi, L. & Janne, P.A. Crizotinib for ALK-rearranged non-small cell lung cancer: a new targeted therapy for a new target. Clinical cancer research : an official journal of the American Association for Cancer Research18, 3737-3742 (2012).
Alamgeer, M., Ganju, V. & Watkins, D.N. Novel therapeutic targets in non-small cell lung cancer. Current opinion in pharmacology13, 394-401 (2013).
Hallberg, B. & Palmer, R.H. Mechanistic insight into ALK receptor tyrosine kinase in human cancer biology. Nature reviews. Cancer13, 685-700 (2013).
Katayama, R. et al. Mechanisms of acquired crizotinib resistance in ALK-rearranged lung Cancers. Science translational medicine4, 120ra117 (2012).
Zou, H.Y. et al. PF-06463922 is a potent and selective next-generation ROS1/ALK inhibitor capable of blocking crizotinib-resistant ROS1 mutations. Proceedings of the National Academy of Sciences of the United States of America112, 3493-3498 (2015).
Ou, S.H., Tan, J., Yen, Y. & Soo, R.A. ROS1 as a 'druggable' receptor tyrosine kinase: lessons learned from inhibiting the ALK pathway. Expert review of anticancer therapy12, 447-456 (2012).

* cited by examiner

*Primary Examiner* — Jean Cornet
(74) *Attorney, Agent, or Firm* — Renner Kenner Greive Bobak Taylor & Weber

(57) ABSTRACT

A compound suitable for treating cancer, in particular NSCLC, inhibits activity of oncogenic ROS1 kinase and ALK kinase. The compound has certain structural components such as a quinoline moiety in the backbone and at least one phenyl-containing moiety in a side chain with a hydrophobic substituent attached to the backbone via an up to 6-membered linking group as well as a further hydrophobic moiety. The presence of the structural components allows for an advantageous interaction with the ROS1 kinase domain and, further, with the ALK kinase domain. Hence, said compound represents a highly promising opportunity for patients bearing ROS1- or ALK-dependent cancer. A composition, in particular a pharmaceutical composition, includes the compound. A method for targeting cancer cells harboring an abnormality in ROS1 gene or ALK gene includes contacting a cell with the compound.

17 Claims, 12 Drawing Sheets

US 9,782,400 B2

ONCOGENIC ROS1 AND ALK KINASE INHIBITOR

TECHNICAL FIELD

The present invention relates to a compound that can, in particular, inhibit ROS1 kinase activity and ALK kinase activity for treating cancer such as lung cancer like ROS1-dependent non-small cell lung cancer or ALK-dependent non-small cell lung cancer as well as compositions such as pharmaceutical compositions comprising said compound. The present invention further provides a method to target cancer cells harboring an abnormality in ROS1 gene or ALK gene.

BACKGROUND OF INVENTION

Lung cancer is the leading cause of cancer-related mortality in China and the world, wherein non-small cell lung cancer (NSCLC), in particular NSCLC adenocarcinoma, accounts for approximately 85% of all cases (Jemal, A. et al., CA: a cancer journal for clinicians, 2009, 59:225-249). There are more than 90 kinds of tyrosine kinases which are related to NSCLC.

Receptor tyrosine kinases (RTKs) are mediators of extracellular signals through activation of downstream signaling pathways including ERK, AKT and/or STAT3 cascades to control cell growth, proliferation, survival and motility pathways. In particular, chromosome rearrangements, gene amplification, and point mutations in respective genes contribute to and/or result in abnormal and constitutive RTK activation which is in turn responsible for initiation and progression of many cancers, including NSCLC. The first targetable RTK identified in NSCLC was the anaplastic lymphoma kinase gene (ALK), wherein chromosomal rearrangements of ALK have been identified amongst which is as most common form the echinoderm microtubule-associated protein-like 4 (EML4)-ALK, i.e. comprising portions of the EML4 gene and the ALK gene, wherein several variants of EML4-ALK gene fusions have been identified. EML4-ALK gene fusions have been found in 3% to 7% of NSCLC (Takeuchi, K. et al., Nature medicine, 2012, 18:378-381, Kwak, E. L. et al., The New England journal of medicine, 2010, 363:1693-1703, Roskoski, R., Jr., Pharmacological research, 2013, 68:68-94). These percentages translate into significant numbers of patients due to the increasing number of NSCLC (Shaw, A. T. et al., Nature, 2013, 13:772-787). Furthermore, additional fusion partners besides EML4 have been identified and, besides, ALK activating point mutations and presence of additional gene copies have been observed in several further cancer types activating the signaling pathways downstream to ALK (Roskoski, R., Jr., Pharmacological research, 2013, 68:68-94). In the majority of cases, ALK chromosome rearrangements are non-overlapping with other gene abnormalities found in NSCLC, i.e. usually abnormalities in ALK and ROS1 gene each define a distinct patient subgroup (Alamgeer, M. et al., Current opinion in pharmacology, 2013, 13:394-401).

Chromosome rearrangement involving the oncogenic c-ros oncogenel (ROS1) RTK were later reported, wherein ROS1 gene has been found to be fused with several gene partners in NSCLC. Approximately 1% to 2% of NSCLC patients harbor multiple kinds of ROS1 chromosome rearrangement (Shaw, A. T. et al., Nature, 2013, 13:772-787). Chromosome rearrangements of either ROS1 or ALK which may be based on interchromosomal translocation or intrachromosomal deletion are accompanied by the fusion of a portion of the ROS1 or ALK protein that includes its entire tyrosine kinase domain with several partner proteins with resulting ROS1 fusion kinases or ALK fusion kinases being constitutively activated and driving cellular transformation (e.g. Lovly, C. M. and Pao, W., Science translational medicine, 2012, 4:1-5). Respective cancers become dependent on continued signaling triggered by said fusion kinases, also named "oncogene addiction" (Shaw, A. T. et al., Nature, 2013, 13:772-787). In particular, ROS1 or ALK fusion kinases activate growth and survival pathways necessary for the growth and survival of cancer cells, which pathways are reported to include auto-phosphorylation of either ROS1 or ALK and phosphorylation of AKT, ERK and STAT3.

Recent developments in targeted-based therapies have led to a major paradigm shift in oncology. Small-molecule tyrosine kinase inhibitors are provided to treat cancer patients who have tyrosine kinase gene fusions, such as ROS1 or ALK chromosome rearrangements. Several tyrosine kinase inhibitors proved to have promising effects in the clinical practice. For example, crizotinib, a potent ATP-competitive small molecule inhibitor of ALK, have now been approved by the FDA for treating NSCLC patients that harbor ALK rearrangements. Crizotinib shows marked anti-tumor activity both in vitro and in vivo as well as in clinical practice. Since the tyrosine kinase domains of ALK and ROS1 are very similar, with 77% identity within the ATP-binding sites, most ALK inhibitors have cross activity against ROS1. In one early clinical trial of crizotinib to treat NSCLC patients harboring ROS1 rearrangements, the objective response rate was 72%, the median duration of response was 17.6 months and median progression-free survival was 19.2 months. Although most patients with ROS1-positive NSCLC exhibit substantial clinical benefit from crizotinib, the efficacy of crizotinib is limited due to the development of drug resistances. Hence, ensuring durable response to crizotinib therapy represents a universal challenge as drug resistance proved to be common and based on several resistance mechanisms in patients treated with crizotinib. Accordingly, patients who responded to crizotinib will eventually experience disease progression despite continued treatment.

Thus, further potent RTK inhibitors for cancer therapy have to be identified. Accordingly, there is a strong need for new compounds which are able to target RTKs and sufficiently inhibit their kinase activity, in particular ROS1 or ALK kinase activity, which compounds can, thus, be used for cancer therapy, in particular for treatment of NSCLC.

SUMMARY OF INVENTION

The first aspect of the present invention relates to a method of treating cancer, i.e. in particular lung cancer such as NSCLC, by a compound of Formula (Ia) in a subject in need thereof, in particular a subject such as a human having an abnormality in either ROS1 gene or ALK gene, in particular a ROS1 chromosome rearrangement or an ALK chromosome rearrangement.

Namely the method of treating a subject suffering from cancer comprises administering an effective amount of a compound having the structure of Formula (Ia) or a pharmaceutically acceptable salt, solvate or anhydrate thereof to the subject:

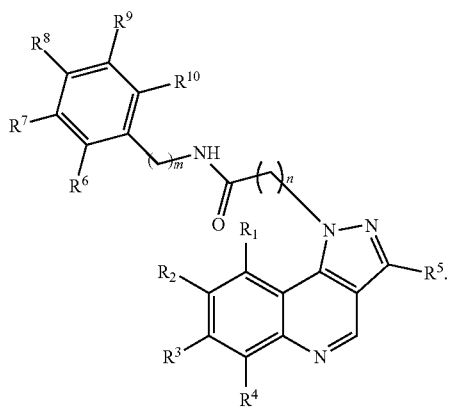

Formula (Ia)

R¹, R², R³ and R⁴ are each independently selected from hydrogen, halogen, $C_1$-$C_3$ haloalkyl, nitro, cyano or $C_1$-$C_3$-alkyl. R⁵ represents a hydrophobic moiety and is selected from optionally substituted $C_6$-$C_{10}$-aryl or optionally substituted $C_7$-$C_{10}$-aralkyl. R⁶, R⁷, R⁸, R⁹ and R¹⁰ are each independently selected from hydrogen, $C_1$-$C_3$-alkoxy or $C_1$-$C_3$-alkylamino, with the provisio that at least one of R⁶, R⁷, R⁸, R⁹ and R¹⁰ is selected from $C_1$-$C_3$-alkoxy or $C_1$-$C_3$-alkylamino, in particular at least R₈ is selected from $C_1$-$C_3$-alkoxy or $C_1$-$C_3$-alkylamino. n and m are each an integer, wherein n is selected from 0, 1, 2 or 3 and m is selected from 0, 1, 2, or 3, wherein the sum of n and m is at least 1 and at most 4.

Hence, the compound of the present invention comprises certain structural components, namely a quinoline moiety in the backbone, i.e. the core part of the compound, at least one phenyl moiety with at least one hydrophobic substituent, which phenyl moiety is attached to the backbone via an at most 6-membered linking group and a further hydrophobic moiety attached to the backbone, namely R₅. The inventors found that such compound of Formula (Ia) is especially suitable for inhibiting ROS1 kinase activity, in particular ROS1 fusion kinase activity. Moreover, the inventors found that the compound of Formula (Ia) having the above mentioned structural components is also exceptionally effective in inhibiting ALK kinase activity, in particular ALK fusion kinase activity.

In particular, the compound has the structure of Formula (Ic):

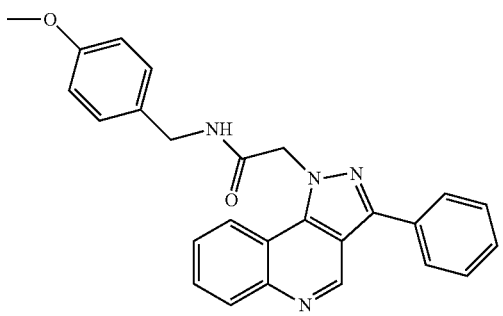

Formula (Ic)

In still another aspect, the present invention refers to a method of inhibiting ROS1 kinase activity, in particular ROS1 fusion kinase activity, or ALK kinase activity, in particular ALK fusion kinase activity, in cancer cells by a compound of Formula (Ia) in a subject in need thereof, i.e. comprising administering an effective amount of the compound of Formula (Ia), in particular of Formula (Ic), to a subject suffering from cancer, in particular lung cancer like NSCLC. In one embodiment the disease is ROS1-dependent NSCLC. In another embodiment, the disease is ALK-dependent NSCLC.

According to the invention is also the compound of Formula (Ia) such as Formula (Ic) for use as a medicament, preferably for use in the treatment of cancer such as NSCLC like ROS1-dependent or ALK-dependent NSCLC. Furthermore, the invention refers to the use of the compound of Formula (Ia) such as Formula (Ic) for preparing a medicament for treatment of a disease, in particular cancer such as NSCLC like ROS1-dependent NSCLC or ALK-dependent NSCLC.

Another aspect of the present invention relates to a composition comprising the compound of Formula (Ia) or a salt, solvate or anhydrate thereof:

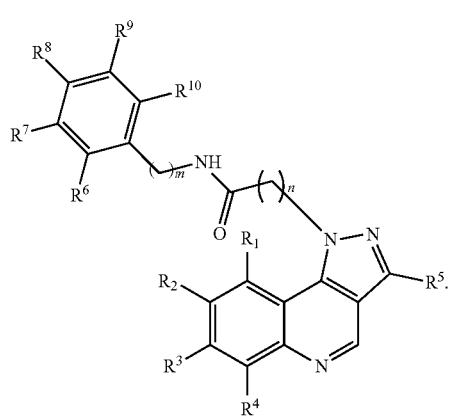

Formula (Ia)

Wherein R¹ to R¹⁰ and n and m are as defined above. In particular the composition is a pharmaceutical composition comprising the compound of Formula (Ia) or a pharmaceutically acceptable salt, solvate or anhydrate thereof. Said pharmaceutical composition further comprises physiologically tolerable excipients and may additionally contain further active ingredients, in particular therapeutic compounds for treating cancer such as NSCLC. The present invention also refers to the use of the composition for inhibiting ROS1 kinase activity or ALK kinase activity, in particular ROS1 fusion kinase activity or ALK fusion kinase activity, such as for suppressing phosphorylation of ROS1 kinase or ALK kinase, in particular ROS1 fusion kinase or ALK fusion kinase, and/or inhibiting the anti-apoptotic and growth signaling downstream to ROS1 kinase or ALK kinase, in particular ROS1 fusion kinase or ALK fusion kinase.

The present invention, in another aspect, refers to a method for targeting cancer cells harboring an abnormality in ROS1 gene or an abnormality in ALK gene, in particular an abnormality in ROS1 gene resulting from a ROS1 chromosome rearrangement such as those associated with the expression of at least one ROS1 fusion kinase including SLC34A2-ROS1 or CD74-ROS1 or an abnormality in ALK gene resulting from an ALK chromosome rearrangement such as those associated with the expression of at least one ALK fusion kinase including EML4-ALK fusion kinases. Said method of the present invention comprises the step of contacting said cells with a compound of Formula (Ia) or a salt, solvate or anhydrate thereof:

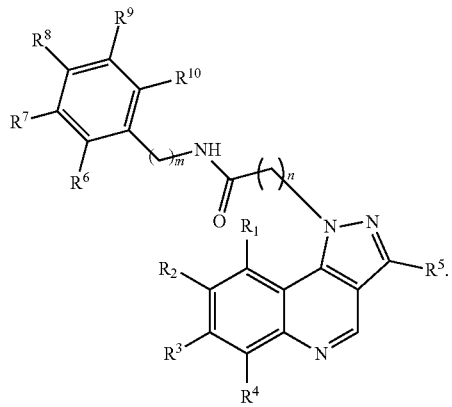

Formula (Ia)

$R^1$ to $R^{10}$ and n and m are as defined above.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF DRAWINGS

FIG. 2A shows a fluorescence image of HCC78 cells having been treated with 2.5 μM crizotinib. FIG. 2B shows a fluorescence image of the control group of HCC78 cells. FIG. 2C shows a fluorescence image of HCC78 cells having been treated with 1.25 μM of the compound of Formula (Ic). FIG. 2D shows a fluorescence image of HCC78 cells having been treated with 2.5 μM of the compound of Formula (Ic). FIG. 2E shows a fluorescence image of HCC78 cells having been treated with 5 μM of the compound of Formula (Ic).

FIG. 3A shows a Flow Cytometry pattern of HCC78 cells having been treated with 2.5 μM crizotinib. FIG. 3B shows a Flow Cytometry pattern of the control group of HCC78 cells. FIG. 3C shows a Flow Cytometry pattern of HCC78 cells having been treated with 1.25 μM of the compound of Formula (Ic). FIG. 3D shows a Flow Cytometry pattern of HCC78 cells having been treated with 2.5 μM of the compound of Formula (Ic). FIG. 3E shows a Flow Cytometry pattern of HCC78 cells having been treated with 5 μM of the compound of Formula (Ic).

FIG. 7A shows a Flow Cytometry pattern of H2228 cells having been treated with 5 μM crizotinib. FIG. 7B shows a Flow Cytometry pattern of the control group of H2228 cells. FIG. 7C shows a Flow Cytometry pattern of H2228 cells having been treated with 1.25 μM of the compound of Formula (Ic). FIG. 7D shows a Flow Cytometry pattern of H2228 cells having been treated with 2.5 μM of the compound of Formula (Ic). FIG. 7E shows a Flow Cytometry pattern of H2228 cells having been treated with 5 μM of the compound of Formula (Ic).

FIG. 8A refers to the formation of H2228 cell colonies after treatment with 5 μM crizotinib. FIG. 8B refers to the formation of H2228 cell colonies in the control group. FIG. 8C refers to the formation of H2228 cell colonies after treatment with 1.25 μM of the compound of Formula (Ic). FIG. 8D refers to the formation of H2228 cell colonies after treatment with 2.5 μM of the compound of Formula (Ic). FIG. 8E refers to the formation of H2228 cell colonies after treatment with 5 μM of the compound of Formula (Ic).

DETAILED DESCRIPTION OF INVENTION

Figure 1A:
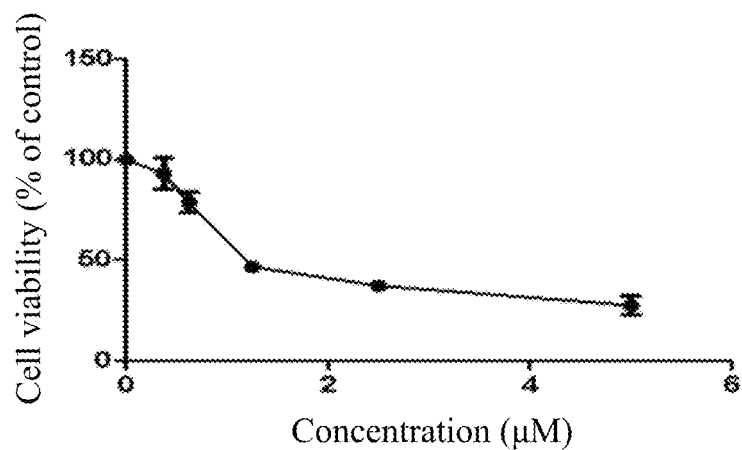
FIG. 1A shows the cell viability of HCC78 cells after 72 hours treatment with the compound of Formula (Ic).

Unless otherwise defined, all technical terms used herein have the same meaning as commonly understood by one skilled in the art to which the invention belongs unless indicated otherwise.

The present invention provides a compound for use in a method for treating cancer in a subject in need thereof. More specifically, the present invention, in a first aspect, refers to a method of treating cancer by a compound in a subject in need thereof, namely a method of treating a subject suffering from cancer comprising administering an effective amount of a compound to the subject. The cancer is, in particular, a NSCLC such as a NSCLC adenocarcinoma, in particular ROS1-dependent NSCLC or ALK-dependent NSCLC.

The term "ROS1-dependent" (or ROS1-positive) as used within this patent application refers to a cancer with cancer cells harboring an abnormality in ROS1 gene. An abnormality in ROS1 gene preferably results from a ROS1 chromosome rearrangement, also referenced as ROS1 gene fusion. "ROS1 chromosome rearrangement" used herein refers to a type of chromosome abnormality such as due to interchromosomal translocation or intrachromosomal deletion, inversion or duplication involving the ROS1 gene, which results in the creation of fusion genes of the rearrangement partner and the ROS1 gene or parts thereof usually associated with the expression of ROS1 fusion kinases containing the whole kinase domain of ROS1 wild-type kinase.

The abnormality in ROS1 gene preferably results from a ROS1 chromosome rearrangement selected from at least one of SLC34A2 (or SCL34A2)-ROS1, CD74-ROS1, CLTC-ROS1, EZR-ROS1, TPM3-ROS1, SDC4-ROS1, LRIG3-ROS1, KDELR2-ROS1, CCDC6-ROS1, LIMA1-ROS1, FIG-ROS1 or MSN-ROS1, more preferably SLC34A2-ROS1 or CD74-ROS1. This also includes respective variants of the aforementioned chromosome rearrangements. Preferably, said abnormality in ROS1 gene is associated with a detectable expression of a ROS1 kinase, if the ROS1 kinase is not expressed in noncancerous cells without abnormality of ROS1 gene of the same cell type, otherwise an increase in the expression of a ROS1 kinase compared to non-cancerous cells of the same cell type. The abnormality in ROS1 gene preferably results from a ROS1 chromosome rearrangement associated with a detectable expression of at least one ROS1 fusion kinase selected from the group consisting of SLC34A2 (or SCL34A2)-ROS1 (including SLC34A2-ROS1(S), SLC34A2-ROS1(L) and SLC34A2-ROS1(VS)), CD74-ROS1, CLTC-ROS1, EZR-ROS1, TPM3-ROS1, SDC4-ROS1, LRIG3-ROS1, KDELR2-ROS1, CCDC6-ROS1, LIMA1-ROS1, FIG-ROS1 (including FIG-ROS1(L), FIG-ROS1(S) and FIG-ROS1(VL)) and MSN-ROS1, more preferably selected from the group consisting of SLC34A2-ROS1 and CD74-ROS1 fusion kinases. In all these fusion kinases, the ROS1 kinase domain of ROS1 wild-type kinase is fully retained. I.e. ROS1-dependent cancer or subjects preferably have a detectable expression of at least one ROS1 fusion kinase, respectively, as a result of the fusion between ROS1 gene and another rearrangement gene.

Accordingly, the term "ALK-dependent" (or ALK-positive) as used herein refers to a cancer with cancer cells harboring an abnormality in ALK gene. The abnormality in ALK gene preferably results from one or more of: an ALK chromosome rearrangement, additional gene copies of the ALK gene or point mutations in the ALK gene itself in particular point mutations in the tyrosine kinase domain, i.e. mutations affecting only one or very few nucleotides in the ALK gene sequence. "ALK chromosome rearrangement" used herein refers to a type of chromosome abnormality such as due to interchromosomal translocation or intrachromosomal deletion, inversion or duplication involving the ALK gene, which results in the creation of fusion genes of the rearrangement partner and the ALK gene usually associated with the expression of ALK fusion kinase containing the whole kinase domain of ALK wild-type kinase.

Most preferably, said abnormality in ALK gene is an ALK chromosome rearrangement, also referenced as ALK gene fusion. Hence, most preferably ALK-dependent means cancer with cells harboring an abnormality in ALK gene, which abnormality in ALK gene results from an ALK chromosome rearrangement. The chromosome rearrangement is, preferably, selected from one or more of EML4-ALK, KIF5B-ALK, KLC1-ALK, PTPN3-ALK, STRN-ALK and TFG-ALK, most preferably EML4-ALK. This also includes respective variants of the aforementioned chromosome rearrangements in particular variants of EML4-ALK chromosome rearrangements which include, for example, EML4-ALK, E13;A20 (variant 1), EML4-ALK, E20;A20 (variant 2), EML4-ALK, E6a/b;A20 (variant 3a/b), EML4-ALK, E14;A20 (variant 4), EML4-ALK, E2a/b;A20 (variant 5a/b), EML4-ALK, E13b;A20 (variant 6), EML4-ALK, E14;A20 (variant 7), EML4-ALK, E15;A20 (variant "V4"), EML4-ALK, E17;A20 and EML4-ALK, E18;A20 (variant "V5"). Variants of KIF5B-ALK include, for example, KIF5B-ALK, K17;A20 or KIF5B-ALK, K24;A20.

Preferably, the abnormality in ALK gene is associated with a detectable expression of an ALK kinase, if the ALK kinase is not expressed in noncancerous cells without abnormality of ALK gene of the same cell type, otherwise an increase in the expression of an ALK kinase compared to non-cancerous cells of the same cell type. Especially preferably, said abnormality in ALK gene is an ALK chromosome rearrangement associated with a detectable expression of at least one ALK fusion kinase in particular selected from the group consisting of EML4-ALK, KIF5B-ALK, KLC1-ALK, PTPN3-ALK, STRN-ALK and TFG-ALK. Most preferably selected from of at least one EML4-ALK fusion kinase in particular at least one EML4-ALK fusion kinase resulting from a variant of EML4-ALK chromosome rearrangement including EML4-ALK, E13;A20 (variant 1), EML4-ALK, E20;A20 (variant 2), EML4-ALK, E6a/b;A20 (variant 3a/b), EML4-ALK, E14;A20 (variant 4), EML4-ALK, E2a/b;A20 (variant 5a/b), EML4-ALK, E13b;A20 (variant 6), EML4-ALK, E14;A20 (variant 7), EML4-ALK, E15;A20 (variant "V4"), EML4-ALK, E17;A20 and EML4-ALK, E18;A20 (variant "V5"), in particular from EML4-ALK, E13;A20 (variant 1), EML4-ALK, E20;A20 (variant 2) or EML4-ALK, E6a/b;A20 (variant 3a/b).

In all these fusion kinases, the ALK kinase domain of ALK wild-type kinase is fully retained. I.e. ALK-dependent cancer or subjects preferably have a detectable expression of at least one ALK fusion kinase, respectively, as a result of the fusion between the ALK gene and another gene.

An "increased expression" of ROS1 kinase or ALK kinase means an expression at least 5% and preferably at least 10% higher than in the control group, i.e. non-cancerous cells without abnormality of ROS1 or ALK gene. The skilled person is aware of suitable methods for determining ROS1 kinase or ALK kinase expression.

ROS1 wild-type kinase or ALK wild-type kinase, its structure as well as ROS1 chromosome rearrangements or ALK chromosome rearrangements and gene fusions, respectively, as well as resulting ROS1 fusion kinases and ALK fusion kinases are known to the skilled person. "ROS1 wild-type kinase" (or -protein) and "ALK wild-type kinase" (or -protein) generally refer to the respective full length protein with the sequence as encoded in normal (healthy) cells or tissue, namely non-cancerous cells or tissue, i.e. without ROS1 or ALK involving chromosome rearrangements. In contrast, "ROS1 fusion kinase" and "ALK fusion kinase" refer to the fusion protein expressed after ROS1 involving chromosome rearrangement or ALK involving chromosome rearrangement, in which at least the kinase domain of the ROS1 wild-type protein or ALK wild-type protein fused to all or a portion of another protein and polypeptide, respectively. For example, SLC34A2-ROS1 is a fusion of a portion of the SLC34A2 polypeptide with a portion of the ROS1 polypeptide based on a gene fusion of respective encoding polynucleotides. The CD74 gene encodes a type 2 transmembrane protein that fuses with ROS1 to generate a CD74-ROS1 transcript found to be the most common form of all ROS1 fusion genes in NSCLC, accounting for about 40% of all ROS1 fusions genes in NSCLC. The terms "ROS1 kinase" and "ALK kinase" generally cover wild-type kinases as well as fusion kinases.

Whether a cancer or a subject is ROS1-dependent or ALK-dependent can be confirmed by respective molecular biological methods, wherein several methods are known to the skilled person. Commonly used and suitable methods especially include fluorescence in situ hybridization (FISH) (i.e. Shaw, A. T. et al., Nature 2013, 13:772-787), immunohistochemistry (IHC) (i.e. Shaw, A. T. et al., Nature 2013, 13:772-787) and quantitative real-time reverse transcription-PCR (qRT-PCR) assays or chromogenic in situ hybridization (CISH) (Gandhi, L. and Jaenne, P. A., Clinical cancer research, 2012, 18:3737-3742). I.e. "ROS1-dependent cancer" or "abnormality in ROS1 gene" is in particular considered for being present when at least one of the methods selected from FISH, IHC, CISH or qRT-PCR assay reveals a ROS1 chromosome rearrangement. Accordingly, "ALK-dependent cancer" or "abnormality in ALK gene" is in particular considered for being present when at least one of the methods selected from FISH, IHC, CISH or qRT-PCR assay reveals an ALK chromosome rearrangement. The same is true with regard to the specific type of ROS1 or ALK chromosome rearrangement, for which methods, in particular fusion partner specific assays, are known to the skilled person, as well.

The cancer is preferably a lung cancer, in particular a ROS1-dependent lung cancer or an ALK-dependent lung cancer. Preferably, the lung cancer is NSCLC. Hence, in especially preferred embodiments of the present invention, the disease is NSCLC, in particular a ROS1-dependent NSCLC or an ALK-dependent NSCLC. The disease is, in particular, NSCLC adenocarcinoma.

The terms "cancer" and "cancerous" refer to or describe a physiological condition in subjects in which a population of cells are characterized by unregulated cell growth. The term "tumor" simply refers to a mass being of benign (generally harmless) or malignant (cancerous) growth.

The method of the present invention comprises administering an effective amount of a compound or a pharmaceutically acceptable salt, solvate or anhydrate thereof to a subject. The subject can be a human or animal, in particular the subject is a human. In preferred embodiments of the present invention, the subject is a mammal having an abnormality in ROS1 gene resulting from ROS1 chromosome rearrangement, which preferably includes ROS1 chromosome rearrangement with the generation of at least one of SLC34A2-ROS1 or CD74-ROS1 fusion kinase. The inventors found that the compound is sufficiently effective in treating subjects with abnormality in ALK gene, as well. Hence, in another embodiment of the present invention, the subject is a mammal having an abnormality in ALK gene resulting from an ALK chromosome rearrangement, which preferably includes ALK chromosome rearrangement with the generation of at least one EML4-ALK fusion kinase, i.e. at least one fusion kinase resulting from a EML4-ALK gene fusion including respective variants, in particular at least one fusion kinase selected from EML4-ALK, E13;A20 (variant 1), EML4-ALK, E20;A20 (variant 2) or EML4-ALK, E6a/b;A20 (variant 3a/b).

The compound of the present invention has a structure of Formula (Ia):

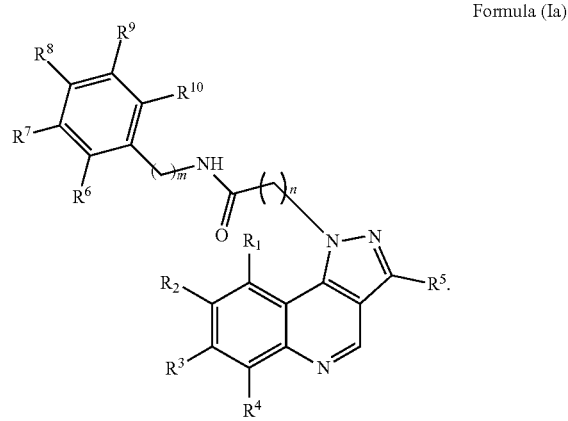

Formula (Ia)

$R^1$, $R^2$, $R^3$ and $R^4$ are each independently selected from hydrogen, halogen, $C_1$-$C_3$ haloalkyl, nitro, cyano or $C_1$-$C_3$-alkyl. In preferred embodiments, $R^1$, $R^2$, $R^3$ and $R^4$ are each independently selected from hydrogen, halogen or $C_1$-$C_2$ haloalkyl. In further preferred embodiments, $R^1$, $R^2$, $R^3$ and $R^4$ are each independently selected from hydrogen, Cl, Br or F, in particular from hydrogen or Cl. In especially preferred embodiments of the present invention, $R^1$, $R^2$, $R^3$ and $R^4$ are all hydrogen.

$R^5$ represents a hydrophobic moiety. $R_5$ is selected from optionally substituted $C_6$-$C_{10}$-aryl or optionally substituted $C_7$-$C_{10}$-aralkyl. Preferably, $R^5$ is selected from $C_6$-$C_{10}$-aryl or $C_7$-$C_{10}$-aralkyl, still more preferably from a $C_6$-$C_{10}$-aryl. In particular embodiments of the present invention, $R^5$ is optionally substituted $C_6$-$C_{10}$-aryl, i.e. $C_6$-$C_{10}$-aryl which may contain further substituents, namely at least one hydrogen atom, in particular one hydrogen atom, is replaced with a substituent, for example, a $C_1$-$C_3$ alkyl, $C_1$-$C_3$ alkoxy, $C_1$-$C_3$ alkylamino, preferably a $C_1$-$C_2$ alkyl, $C_1$-$C_2$ alkoxy or a $C_1$-$C_2$ alkylamino. Still more preferably, $R^5$ is optionally substituted phenyl, wherein at least one hydrogen atom, in particular one hydrogen atom, is optionally replaced with a substituent, preferably a $C_1$-$C_3$ alkyl, $C_1$-$C_3$ alkoxy or a $C_1$-$C_3$ alkylamino, more preferably a $C_1$-$C_2$ alkyl, $C_1$-$C_2$ alkoxy or a $C_1$-$C_2$ alkylamino, still more preferably a $C_1$-$C_2$ alkoxy. Still more preferably, $R^5$ is a moiety having the structure:

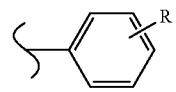

In said embodiments, R is hydrogen, a $C_1$-$C_2$ alkyl, $C_1$-$C_2$ alkoxy or a $C_1$-$C_2$ alkylamino. Most preferably, R is hydrogen, i.e. the phenyl is unsubstituted. Accordingly, in especially preferred embodiments of the present invention, $R^5$ is $C_6$-$C_{10}$-aryl, i.e. unsubstituted $C_6$-$C_{10}$-aryl, and in particular phenyl, i.e. unsubstituted $C_6$ aryl.

$R^6$, $R^7$, $R^8$, $R^9$ and $R^{10}$ are each independently selected from hydrogen, $C_1$-$C_3$-alkoxy or $C_1$-$C_3$-alkylamino, with the provisio that at least one of $R^6$, $R^7$, $R^8$, $R^9$ and $R^{10}$ is selected from $C_1$-$C_3$-alkoxy or $C_1$-$C_3$-alkylamino, preferably at least $R_8$ is selected from $C_1$-$C_3$-alkoxy or $C_1$-$C_3$-alkylamino. Still more preferably, $R^6$, $R^7$, $R^8$, $R^9$ and $R^{10}$ are each independently selected from hydrogen or $C_1$-$C_3$-alkoxy, with the provisio that at least one of $R^6$, $R^7$, $R^8$, $R^9$ and $R^{10}$ is selected from $C_1$-$C_3$-alkoxy. In particular, $R^6$, $R^7$, $R^8$, $R^9$ and $R^{10}$ are each independently selected from hydrogen or $C_1$-$C_2$-alkoxy, with the provisio that at least one of $R^6$, $R^7$, $R^8$, $R^9$ and $R^{10}$ is $C_1$-$C_2$-alkoxy. More preferably, $R^6$, $R^7$, $R^8$, $R^9$ and $R^{10}$ are each independently selected from hydrogen or methoxy, with the provisio that at least one of $R^6$, $R^7$, $R^8$, $R^9$ and $R^{10}$ is methoxy. In an especially preferred embodiment of the present invention, $R^6$, $R^7$, $R^9$ and $R^{10}$ are hydrogen and $R^8$ is $C_1$-$C_2$-alkoxy, in particular methoxy.

n and m are an integer and each indicate the number of methylene groups. For example, if n is 0, there is no methylene group present at the respective position, i.e. the carbonyl-group is directly bonded to the nitrogen atom in the pyrazole ring structure. In case of n=1, there is one methylene group connecting the carbonyl group with the nitrogen atom in the pyrazole ring structure. n is selected from 0, 1, 2 or 3 and m is selected from 0, 1, 2 or 3, wherein the sum of n and m is at least 1 and at most 4. More preferably, the sum of n and m is at most 3 and in particular at most 2, most preferably the sum of n and m is 2. n is preferably selected from 0, 1 or 2 and m is preferably selected from 1, 2 or 3. In especially preferred embodiments, n and m are both 1.

The term "optionally substituted" as used herein means that said radical or group is either unsubstituted or substituted. "Substituted" means that one or more hydrogen atoms of that radical or group, preferably one to two hydrogen atoms, in particular one hydrogen atom, are replaced with certain substituents provided that the normal valency is not exceeded and that the substitution results in a chemically stable compound. For example, optionally substituted $C_7$-$C_{10}$-aralkyl means that the radial may be substituted at the aryl ring or not. Use of the term $C_7$-$C_{10}$-aralkyl without the expression "optionally substituted" is to be understood to refer to unsubstituted $C_7$-$C_{10}$-aralkyl, only. This also applies with regard to the term "optionally substituted $C_6$-$C_{10}$-aryl" versus "$C_6$-$C_{10}$-aryl".

The term "$C_1$-$C_3$ alkyl" as group used in the present invention refers to a hydrocarbyl radical having from 1 to 3 carbon atoms which includes a straight chain or branched alkyl group. Namely, it comprises methyl, ethyl, propyl and isopropyl. Likewise, "$C_1$-$C_2$ alkyl" refers to a hydrocarbyl radical having 1 to 2 carbon atoms.

"$C_1$-$C_3$ alkoxy" refers to a radical having a formula -AB wherein A is an oxygen atom and B is $C_1$-$C_3$ alkyl, i.e. including methoxy, ethoxy, propoxy and isopropyloxy. "$C_1$-$C_2$ alkoxy" refers to a radical having a formula -AB wherein A is an oxygen atom and B is $C_1$-$C_2$ alkyl, i.e. including methoxy and ethoxy.

The term "$C_1$-$C_3$ alkylamino" refers to a radical having a formula —$NB_xH_y$, wherein x and y are selected from among x=1, y=1 and x=2, y=0. B is a $C_1$-$C_3$ alkyl, i.e. the number of carbon atoms in B is 1 to 3. When x=2, the total number of carbon atoms of both B groups is from 1 to 3. "$C_1$-$C_3$ alkylamino" includes N-methylamino-, N,N-dimethylamino- and N-ethylamino- or N-ethyl-N-methylamino-. "$C_1$-$C_2$ alkylamino" likewise refers to a radical having a formula —$NB_xH_y$, wherein x and y are as defined above and B is a $C_1$-$C_2$ alkyl, i.e. the number of carbon atoms in B is 1 to 2.

The term "$C_7$-$C_{10}$ aralkyl" refers to an alkyl radical with an aryl ring, i.e. a radical having a formula -AB, wherein A is a branched or straight chain hydrocarbyl radical and B is an aryl ring, usually a phenyl ring, attached to the hydrocarbyl radical, both in total comprise from 7 to 10 carbon atoms. Examples of such groups include benzyl (i.e. phenylmethyl), phenethyl, phenylpropyl, phenylbutyl. The "$C_7$-$C_{10}$ aralkyl" is optionally substituted, i.e. at least one hydrogen atom, in particular one hydrogen atom, may be replaced with a substituent, for example, selected from a $C_1$-$C_3$ alkyl, $C_1$-$C_3$ alkoxy or $C_1$-$C_3$ alkylamino.

"$C_6$-$C_{10}$ aryl" according to the invention means an hydrocarbon residue with 6 to 10 carbon atoms having a ring with a maximum number of double bonds, i.e. the maximum number of u electrons, in particular an aromatic ring, and includes monocyclic and polycyclic hydrocarbons wherein the additional ring(s) of the polycyclic hydrocarbon may be saturated, i.e. without double or triple bonds, unsaturated or aromatic. "Unsaturated" means the presence of at least one double or triple bond. "Aromatic" means the presence of a delocalized, conjugated π-electron system, namely the term "aromatic" generally means a ring having a delocalized π-electron system containing 4n+2π electrons, where n is an integer and at least 0. Most preferably, $C_6$-$C_{10}$ aryl refers to an aromatic hydrocarbon with 6 to 10 carbon atoms, more preferably with 6 carbon atoms. The $C_6$-$C_{10}$ aryl is optionally substituted; i.e. it may contain further substituents, namely at least one hydrogen atom, in particular one hydrogen atom, is replaced with a substituent, for example, a $C_1$-$C_3$ alkyl, $C_1$-$C_3$ alkoxy or $C_1$-$C_3$ alkylamino, preferably a $C_1$-$C_2$ alkyl, $C_1$-$C_2$ alkoxy or a $C_1$-$C_2$ alkylamino. Examples of "$C_6$-$C_{10}$ aryl" include phenyl, indenyl and naphthyl.

"Nitro" refers to a —$NO_2$ group, wherein "cyano" refers to a —CN group. The term "halogen" as a group or part of a group refers to fluoro (—F), chloro (—Cl), bromo (—Br), iodo (—I) unless otherwise indicated.

The term "$C_1$-$C_3$ haloalkyl" as used herein as a group refers to a straight chain or branched alkyl group with 1 to 3 carbon atoms, wherein one or more hydrogen atoms are replaced with a halogen, in particular one hydrogen atom is substituted with a halogen. Examples of such groups include fluoroethyl, fluoromethyl, trifluoromethyl or trifluoroethyl and the like.

Also contemplated by the present invention are any pharmaceutically acceptable salts, anhydrates, solvates, anhydrates as well as enantiomers and their mixtures, stereoisomeric forms, racemates, diastereomers and their mixtures of the compound of Formula (Ia).

As used herein, the term "solvate" refers to a complex of variable stoichiometry formed by a solute, i.e. compound of Formula (Ia), and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms enantiomers, stereoisomeric forms, racemates, diastereomers are known to the skilled person.

Said compound of Formula (Ia) is, amongst others, characterized by certain structural components, which were found to unexpectedly contribute to an advantageous inhibition of the activity of ROS1 receptor tyrosine kinase by interacting with amino acids within the ROS1 kinase domain and ROS1 binding pocket, respectively. Namely the compound of the present invention comprises a quinoline moiety in the backbone, at least one phenyl containing moiety in a side chain attached to said backbone via an at most 6-membered linking group having at least one hydrophobic substituent as well as a hydrophobic moiety attached to the backbone referenced as $R^5$. Further moieties which may be attached to the backbone or side chain according to Formula (Ia) do not impede the interaction of compound of Formula (Ia) with the ROS1 kinase domain and preferably allow for additional interactions including van der Waals forces and hydrogen bonds or hydrophobic interactions with the ROS1 kinase domain and, thus, further contribute to the exceptional interaction with ROS1 kinase.

The inventors unexpectedly found that the presence of these structural components allows for advantageous multiple interactions with the ROS1 tyrosine kinase domain, in particular the substituted phenyl moiety in the side chain and $R^5$ contribute to advantageous and close hydrophobic interactions with the hinge region and the G-loop in addition to hydrogen bonds in particular with e.g. Met2029 formed by the quinoline moiety. These interactions are considered for being important ones allowing for the advantageous interaction with the ROS1 kinase domain and a potent inhibition of the activity of ROS1 kinase and, hence, ROS1 fusion kinases as said ROS1 kinase domain is fully retained in known fusion partners, i.e. in known ROS1 fusion kinases.

The inventors further found that the compound of Formula (Ia) with those structural components, such as the compound of Formula (Ic), is also exceptionally suitable to inhibit ALK kinase activity such as ALK fusion kinase activity. They found that said compound can advantageously interact with and, thus, bind to the ALK kinase domain based on multiple interactions, too. Such interactions proved to allow for sufficiently and exceptionally inhibiting the ALK phosphorylation and anti-apoptotic and growth signaling downstream to ALK, too. In this context, the structural components of the compound of Formula (Ia) proved to allow for forming hydrogen bonds, e.g. with Met1199 as backbone residue in the hinge region, and for further advantageous interactions with the ALK kinase domain, in particular it fills lipophilic pockets formed by residues of the hinge region and the catalytic spine.

In especially preferred embodiments, the compound is a compound of Formula (Ib):

Formula (Ib)

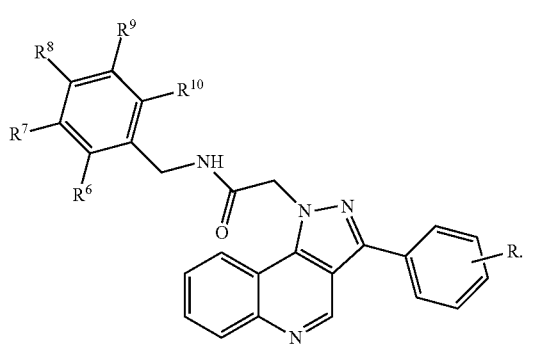

R is hydrogen, a $C_1$-$C_2$ alkyl, a $C_1$-$C_2$ alkoxy or a $C_1$-$C_2$ alkylamino. Most preferably, R is hydrogen, i.e. the phenyl is unsubstituted, i.e. has no further substituent.

$R^6$, $R^7$, $R^8$, $R^9$ and $R^{10}$ are each independently selected from hydrogen, $C_1$-$C_2$-alkoxy or $C_1$-$C_2$-alkylamino, with the provisio that at least one of $R^6$, $R^7$, $R^8$, $R^9$ and $R^{10}$ is selected from $C_1$-$C_2$-alkoxy or $C_1$-$C_2$-alkylamino, preferably at least $R_8$ is selected from $C_1$-$C_2$-alkoxy or $C_1$-$C_2$-alkylamino. In particular, $R^6$, $R^7$, $R^8$, $R^9$ and $R^{10}$ are each independently selected from hydrogen or $C_1$-$C_2$-alkoxy, with the provisio that at least one of $R^6$, $R^7$, $R^8$, $R^9$ and $R^{10}$ is $C_1$-$C_2$-alkoxy. More preferably, $R^6$, $R^7$, $R^8$, $R^9$ and $R^{10}$ are each independently selected from hydrogen or methoxy, with the provisio that at least one of $R^6$, $R^7$, $R^8$, $R^9$ and $R^{10}$ is methoxy. In an especially preferred embodiment, $R^6$, $R^7$, $R^9$ and $R^{10}$ are hydrogen and $R^8$ is $C_1$-$C_2$-alkoxy, in particular methoxy.

In particular embodiments of the present invention, the compound is a compound of Formula (Ic):

Formula (Ic)

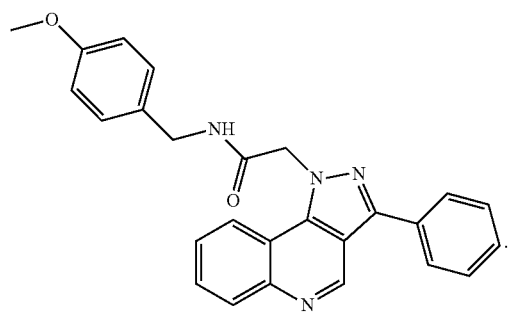

which is also referenced as "G341-0312" herein and includes any pharmaceutically acceptable salt, hydrate, solvate, anhydrate as well as enantiomer and their mixtures, stereoisomeric form, racemate, diastereomer and their mixtures of the compound of Formula (Ic).

As further shown below, respective data with HCC78 cell lines with ROS1 chromosome rearrangement as well as with H2228 cell lines with ALK chromosome rearrangement further confirm that compound of Formula (Ic) is especially effective in inhibiting ROS1 kinase activity and ALK kinase activity. The compound of Formula (Ic) proved to be highly cytotoxic and selective to cancer cells. It proved to advantageously target ROS1 fusion kinase and ALK fusion kinase, respectively, while showing relatively low toxicity to normal lung cells. In particular, the compound of Formula (Ic) proved to exceptionally inhibit growth, induce apoptosis and suppress the phosphorylation of ROS1 fusion kinase while making use of the NSCLC cell line HCC78, which is a NSCLC cell line characterized by ROS1-driven activated signaling due to the presence of the SLC34A2-ROS1 fusion gene. Moreover, the compound of Formula (Ic) proved to exceptionally inhibit growth, induce apoptosis and suppress the phosphorylation of ALK fusion kinase while making use of the NSCLC cell line H2228, which is a NSCLC cell line characterized by the ALK rearrangement EML4-ALK (variant 3). The compound of Formula (Ic) further proved to be highly cytotoxic and selective to cancer cells while having little effect on healthy normal non-cancerous cells.

The expression "effective amount" generally denotes an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells, in particular inhibition, reduction or prevention of the proliferation of the cancer cells or induction of cell death, i.e. apoptosis of the cancer cells.

The effective amount of the compound of Formula (Ia) may depend on the species, body weight, age and individual conditions and can be determined by standard procedures such as with cell cultures or experimental animals. The concentration of the compound of Formula (Ia), such as the compound of Formula (Ic), effective for treating the subject may, for example, be at least 1.25 µM, preferably at least 2.5 µM, in particular at least 5 µM.

The compound of Formula (Ia) has an $IC_{50}$ on cancer cells of at most 10 µM and an $IC_{50}$ on normal non-cancerous cells being at least 1.5 times higher, more preferably 2 times higher, most preferably at least 2.5 times higher than the $IC_{50}$ on cancer cells.

In embodiments of the present invention, the disease is ROS1-dependent NSCLC and the subject suffering from NSCLC has an abnormality in ROS1 gene, respectively, and the compound has an $IC_{50}$ on said NSCLC cells of at most 10 µM and an $IC_{50}$ on normal lung cells being at least 2 times higher, preferably at least 2.5 times higher than the $IC_{50}$ on the NSCLC cells.

In other embodiments of the present invention, the compound is a compound of Formula (Ic) and the disease is ROS1-dependent NSCLC.

In another embodiment of the present invention, the disease is ALK-dependent NSCLC and the subject suffering from NSCLC has an abnormality in ALK gene, respectively, and the compound has an $IC_{50}$ on said NSCLC cells of at most 10 µM and an $IC_{50}$ on normal lung cells being at least 2 times higher than the $IC_{50}$ on the NSCLC cells.

In still further embodiments of the present invention, the compound is a compound of Formula (Ic) and the disease is ALK-dependent NSCLC.

The method of the present invention may further include steps carried out before administering the compound of Formula (Ia), such as compound of Formula (Ic), to the subject comprising:
  Obtaining a sample, in particular cancer cells, from the subject;
  Testing said sample for the level of expression of at least one ROS1 fusion kinase or identifying at least one ROS1 chromosome rearrangement and/or testing said sample for the level of expression of at least one ALK fusion kinase or identifying at least one ALK chromosome rearrangement;
  Optionally correlating the level of ROS1 fusion kinase and/or ALK fusion kinase with outcome and if conditions are met, administrating the compound of Formula (Ia), in particular compound of Formula (Ic), to said subject.

According to the invention is also the compound of Formula (Ia), in particular the compound of Formula (Ib) or (Ic), for use as a medicament, preferably for use in the treatment of cancer such as lung cancer, especially NSCLC, in particular ROS1-dependent cancer or ALK-dependent cancer, especially ROS1-dependent NSCLC or ALK-dependent NSCLC. The compound of Formula (Ia), in particular the compound of Formula (Ib) or (Ic), can be used in an effective amount for treating a human. Another aspect of the invention refers to the use of the compound of Formula (Ia), in particular the compound of Formula (Ib) or (Ic), for preparing a medicament for treatment of a disease, in particular of cancer, especially lung cancer, in particular NSCLC, especially ROS1-dependent NSCLC or ALK-dependent NSCLC.

The compound of Formula (Ia) may be used in combination with other therapeutic compounds, preferably therapeutic compounds which are used for treating cancer such as lung cancer, especially NSCLC.

In still another aspect, the present invention refers to a method for inhibiting ROS1 kinase activity, in particular ROS1 fusion kinase activity, or ALK kinase activity, in particular ALK fusion kinase activity, in cancer cells by a compound of Formula (Ia) in a subject in need thereof, i.e. comprising administering an effective amount of a compound of Formula (Ia), in particular of Formula (Ib) or (Ic), to a subject suffering from a disease such as cancer, in particular lung cancer like NSCLC. In one embodiment of the present invention, the disease is ROS1-dependent NSCLC. In another embodiment of the present invention, the disease is ALK-dependent NSCLC.

A further aspect of the present invention relates to a composition comprising the compound of Formula (Ia) or a salt, solvate or anhydrate thereof:

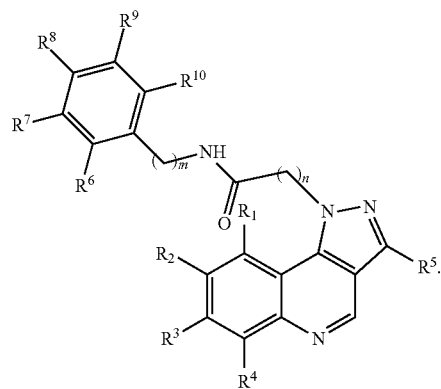

Formula (Ia)

Wherein $R^1$ to $R^{10}$ and n and m are as defined above. The composition further comprises excipients such as pharmaceutically acceptable excipients, a buffer, salt, water or a combination thereof. In particular the composition is a pharmaceutical composition comprising the compound of Formula (Ia) or a pharmaceutically acceptable salt, solvate or anhydrate thereof. Said pharmaceutical composition further comprises physiologically tolerable excipients and may additionally contain further active ingredients, in particular therapeutic compounds for treating cancer such as NSCLC.

The skilled person is able to select suitable excipients depending on the form of the pharmaceutical composition and is aware of methods for manufacturing pharmaceutical compositions as well as able to select a suitable method for preparing the pharmaceutical composition depending on the kind of excipients and the form of the pharmaceutical composition. The pharmaceutical composition according to the invention can be present in solid, semisolid or liquid form to be administered by an oral, rectal, topical, parenteral or transdermal or inhalative route to a subject, preferably a human.

More preferably, the compound in the composition is a compound of Formula (Ib):

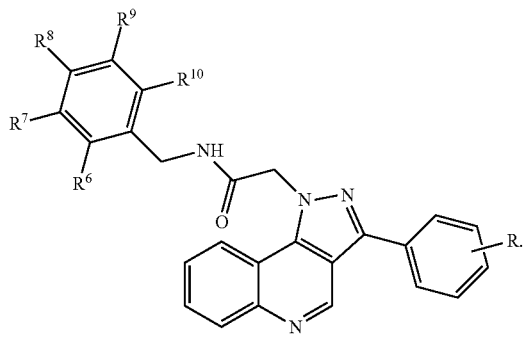

Formula (Ib)

R is hydrogen, a $C_1$-$C_2$ alkyl, $C_1$-$C_2$ alkoxy or a $C_1$-$C_2$ alkylamino. Most preferably, R is hydrogen, i.e. the phenyl is unsubstituted, i.e. has no further substituent.

$R^6$, $R^7$, $R^8$, $R^9$ and $R^{10}$ are each independently selected from hydrogen, $C_1$-$C_2$-alkoxy or $C_1$-$C_2$-alkylamino, with the provisio that at least one of $R^6$, $R^7$, $R^8$, $R^9$ and $R^{10}$ is selected from $C_1$-$C_2$-alkoxy or $C_1$-$C_2$-alkylamino, preferably at least $R_8$ is selected from $C_1$-$C_2$-alkoxy or $C_1$-$C_2$-alkylamino. In particular, $R^6$, $R^7$, $R^8$, $R^9$ and $R^{10}$ are each independently selected from hydrogen or $C_1$-$C_2$-alkoxy, with the provisio that at least one of $R^6$, $R^7$, $R^8$, $R^9$ and $R^{10}$ is $C_1$-$C_2$-alkoxy. More preferably, $R^6$, $R^7$, $R^8$, $R^9$ and $R^{10}$ are each independently selected from hydrogen or methoxy, with the provisio that at least one of $R^6$, $R^7$, $R^8$, $R^9$ and $R^{10}$ is methoxy. In an especially preferred embodiment, $R^6$, $R^7$, $R^9$ and $R^{10}$ are hydrogen and $R^8$ is $C_1$-$C_2$-alkoxy, in particular methoxy.

Especially preferably, the compound in the composition is a compound having Formula (Ic) or a salt, solvate or anhydrate thereof:

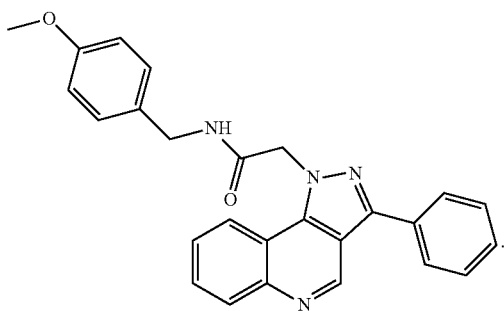

Formula (Ic)

The present invention also refers to the use of the composition such as the pharmaceutical composition for inhibiting ROS1 kinase activity or ALK kinase activity, in particular ROS1 fusion kinase activity or ALK fusion kinase activity, such as for suppressing phosphorylation of ROS1 kinase or ALK kinase, in particular ROS1 fusion kinase or ALK fusion kinase, and/or inhibiting the anti-apoptotic and growth signaling downstream to ROS1 kinase or ALK kinase, in particular ROS1 fusion kinase or ALK fusion kinase.

The present invention in another aspect refers to a method for targeting cancer cells harboring an abnormality in ROS1 gene or harboring an abnormality in ALK gene. Said abnormality in ROS1 gene is in particular a ROS1 chromosome rearrangement. More preferably, the cancer cells express at least one ROS1 fusion kinase selected from SLC34A2-ROS1 or CD74-ROS1. Said abnormality in ALK gene is preferably an ALK chromosome rearrangement, preferably the cancer cells express at least one ALK fusion kinase selected from an EML4-ALK fusion kinase, in particular selected from EML4-ALK, E13;A20 (variant 1), EML4-ALK, E20;A20 (variant 2) or EML4-ALK, E6a/b;A20 (variant 3a/b). The cancer cells are preferably from a lung tumor, more preferably from a NSCLC in particular from a NSCLC adenocarcinoma.

Said method of the present invention comprises the step of contacting said cells with a compound of Formula (Ia) or a salt, solvate or anhydrate thereof:

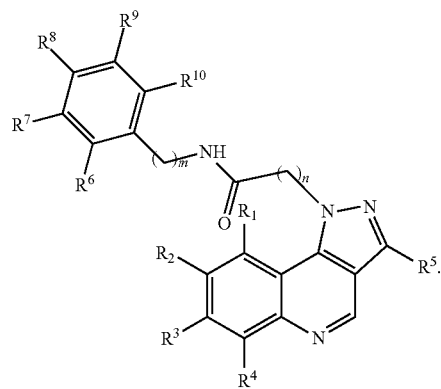

Formula (Ia)

$R^1$ to $R^{10}$ and n and m are as defined above.

Preferably, the proliferation of the cancer cells is inhibited, reduced or prevented or apoptosis of the cancer cells is induced.

Preferably, the cancer cells are contacted with the compound of Formula (Ia) for at least 12 h, more preferably for at least 24 h. The compound of Formula (Ia) is preferably used in a concentration of at least 1.25 µM, more preferably of at least 2.5 µM and especially preferably of at least 5 µM for contacting the cells. The cancer cells contacted with the compound of Formula (Ia) may comprise between $1.0 \times 10^3$ cells and $1.0 \times 10^6$ cells, in particular about $1.0 \times 10^6$ cells.

The compound of Formula (Ia) has an $IC_{50}$ on cancer cells of at most 10 µM and an $IC_{50}$ on normal non-cancerous cells being at least 1.5 times higher, preferably at least 2 times higher, more preferably at least 2.5 times higher than the $IC_{50}$ on cancer cells.

In embodiments of the present invention, the cancer cells are from NSCLC and harbor an abnormality in ROS1 gene being a ROS1 chromosome rearrangement and the compound has an $IC_{50}$ on the cancer cells of at most 10 µM and an $IC_{50}$ on normal non-cancerous lung cells being at least 2 times higher, preferably at least 2.5 times higher than the $IC_{50}$ on the cancer cells.

In another embodiment of the present invention, the cancer cells are from NSCLC and harbor an abnormality in ALK gene being an ALK chromosome rearrangement and the compound has an $IC_{50}$ on the cancer cells of at most 10 µM and an $IC_{50}$ on normal non-cancerous lung cells being at least 2 times higher than the $IC_{50}$ on the cancer cells.

Still more preferably, the compound used for contacting said cells is a compound having Formula (Ib):

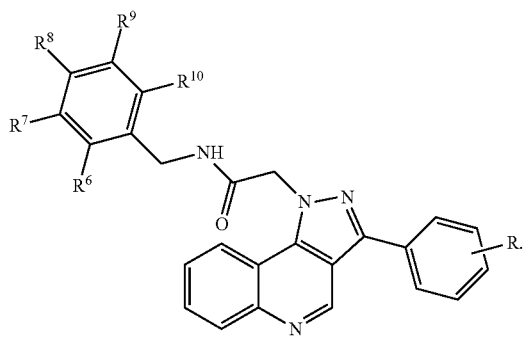

Formula (Ib)

R is hydrogen, a $C_1$-$C_2$ alkyl, a $C_1$-$C_2$ alkoxy or a $C_1$-$C_2$ alkylamino. Most preferably, R is hydrogen, i.e. the phenyl is unsubstituted, i.e. has no further substituent.

$R^6$, $R^7$, $R^8$, $R^9$ and $R^{10}$ are each independently selected from hydrogen, $C_1$-$C_2$-alkoxy or $C_1$-$C_2$-alkylamino, with the provisio that at least one of $R^6$, $R^7$, $R^8$, $R^9$ and $R^{10}$ is selected from $C_1$-$C_2$-alkoxy or $C_1$-$C_2$-alkylamino, preferably at least $R_8$ is selected from $C_1$-$C_2$-alkoxy or $C_r$-$C_2$-alkylamino. In particular, $R^6$, $R^7$, $R^8$, $R^9$ and $R^{10}$ are each independently selected from hydrogen or $C_1$-$C_2$-alkoxy, with the provisio that at least one of $R^6$, $R^7$, $R^8$, $R^9$ and $R^{10}$ is $C_1$-$C_2$-alkoxy. More preferably, $R^6$, $R^7$, $R^8$, $R^9$ and $R^{10}$ are each independently selected from hydrogen or methoxy, with the provisio that at least one of $R^6$, $R^7$, $R^8$, $R^9$ and $R^{10}$ is methoxy. In an especially preferred embodiment, $R^6$, $R^7$, $R^9$ and $R^{10}$ are hydrogen and $R^8$ is $C_1$-$C_2$-alkoxy, in particular methoxy.

Especially preferably, the compound used for contacting said cells is a compound having Formula (Ic) or a salt, solvate or anhydrate thereof:

Formula (Ic)

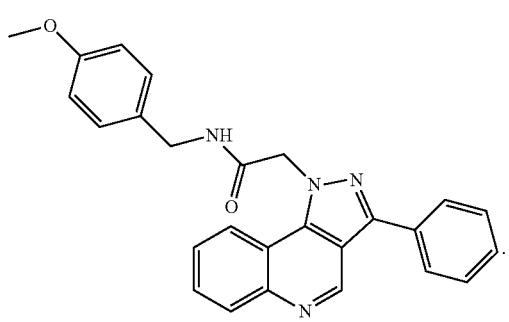

wherein the concentration of compound (Ic) for contacting the cells is at least 2.5 μM, in particular at least 5 μM.

The skilled person is able to prepare the compound of Formula (Ia), in particular of Formula (Ib) or (Ic), with suitable purity and/or respective compounds are commercially available with sufficient purity.

EXAMPLES

Example 1

Inhibition of ROS1 Kinase

The efficiency of the compound of Formula (Ic) as inhibitor of ROS1 has been evaluated. First of all, the cytotoxic properties of the compound of Formula (Ic) with regard to cells with ROS1 chromosome rearrangement and its selectivity towards those cancer cells have been analyzed, its efficacy in inducing cell deaths and inhibition of colony formation in those cells as well as the effects on the ROS1 phosphorylation and anti-apoptotic and growth signaling pathways downstream to ROS1. In the below examples, differences are analyzed by one-way ANOVA.

All statistical analyses are carried out using Graph Prim5.0. Values of $P<0.05$ were considered statistically significant.

Example 1A

Cytotoxic Effects of the Compound of Formula (Ic) Towards Cells with ROS1 Chromosome Rearrangement To show the highly cytotoxic and selective properties of the present compound of Formula (Ic), HCC78 NSCLC cells and normal lung epithelial cells (BEAS-2B) were treated with the compound of Formula (Ic) and respective effects were observed. HCC78 NSCLC cells are non-small cell lung cancer cells with a ROS1 gene fusion. HCC78 cells were obtained from the American Type Culture Collection (ATCC) and cultured in environment of 5% $CO_2$ at 37° C. in RPMI-1640 medium supplemented with 10% fetal bovine serum (FBS), 100 units/mL penicillin, and 100 μg/mL streptomycin. The compound of Formula (Ic) was dissolved in DMSO. Using a MTT assay, 3000 HCC78 or BEAS-2B cells were seeded on 96-well plates, cultured overnight for cell adhesion, and treated with DMSO or various concentrations of the compound of Formula (Ic) for 72 h. Three independent tests were performed. 10 μL of MTT (5 mg/mL; Sigma) were added to each well, and incubation continued for another 4 h. Then the dark blue crystals were dissolved in 100 μL of the resolved solution (10% SDS and 0.1 mM HCL). The absorbance was measured at 570 nm by a microplate reader (Tecan, Morrisville, N.C., USA).

Figure 1B:
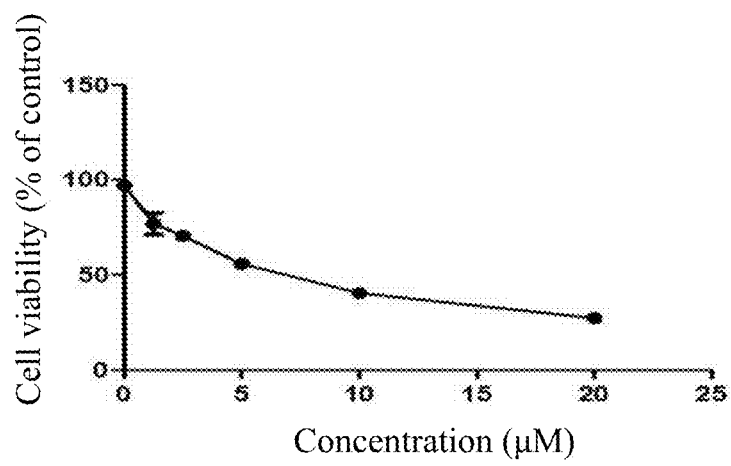
FIG. 1B shows the cell viability of BEAS-2B cells after 72 hours treatment with the compound of Formula (Ic).
Figure 2A:
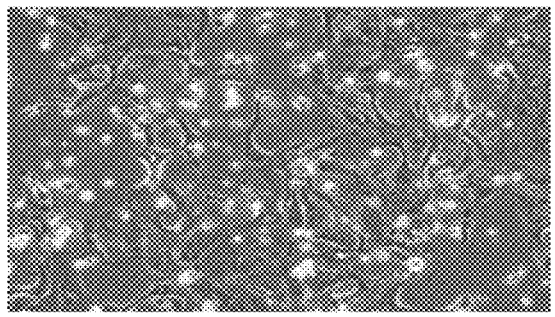
FIG. 2A to 2E show fluorescence images of HCC78 cells having been treated with different concentrations of the compound of Formula (Ic), with crizotinib or the control group.
Figure 2B:
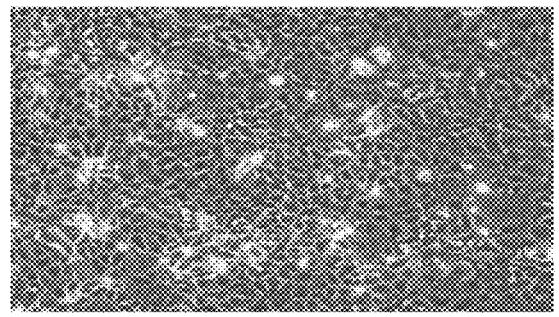
Figure 2C:
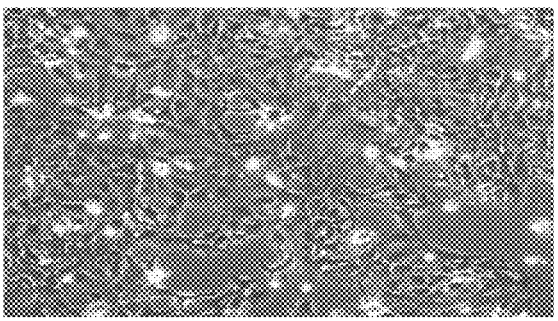
Figure 2D:
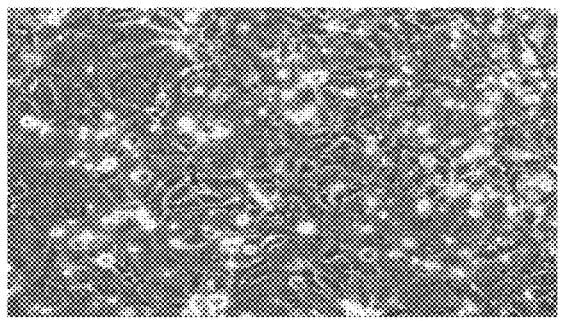
Figure 2E:
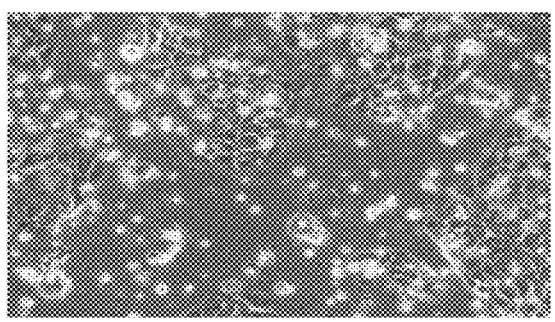

The cell viability was calculated relative to untreated controls, with results based on at least three independent experiments. The MTT assay showed that the compound of Formula (Ic) is a potent inhibitor of HCC78 cells with a $IC_{50}$ of 1.62 μM±0.39 μM, while it showed much lower cytotoxicity on normal lung epithelial cells (BEAS-2B) after 72 h treatment (FIG. 1A and FIG. 1B and table 1). The compound of Formula (Ic) exerts a 3.75-fold cytotoxicity towards cancer cells than normal healthy cells. The present compound of Formula (Ic), thus, proved to be highly selectively towards cancer cells.

TABLE 1

| $IC_{50}$ of the compound of Formula (Ic) | |
|---|---|
| Cell lines | $IC_{50}$ (μM) |
| HCC78 | 1.62 μM ± 0.39 |
| BEAS-2B | 6.08 μM ± 1.16 |

Example 1B

Induction of Apoptosis in HCC78 Cells by the Compound of Formula (Ic)

The compound of Formula (Ic) of the present invention, as a potent ROS1 inhibitor, proved to induce apoptosis in cancerous cells. Apoptosis assay was performed on HCC78 cells to demonstrate the potent ROS1 inhibitory effect of the present invention. HCC78 cells ($1.0 \times 10^5$ cells/well) were allowed to attach to a 6-well plate for 24 h, and the cells were treated with the various concentrations of the compound of Formula (Ic) for additional 72 h. At the end of incubation, the cells were harvested by trypsinization and washed twice with ice-cold PBS. After centrifugation and removal of the supernatants, cell pellets were resuspended in 100 μL 1× Annexin-binding buffer, 2 μL Annexin-V FITC and 2 μL PI (100 μg/ml) were added and incubated in the dark at room temperature for 15 min before further addition of 400 μL of 1× Annexin-binding buffer. The stained cells were analyzed quantitatively using a flow cytometer (BD Biosciences, San Jose, Calif., USA). FIG. 2A to FIG. 2E show fluorescence images of HCC78 cells having been treated with the compound of Formula (Ic) at 1.25 μM, 2.5 μM and 5 μM; 2.5 μM Crizotinib (a known ROS1 inhibitor as positive control) and DMSO (control, negative control). The results show that HCC78 cells having been treated with the compound of Formula (Ic) detach from the surface and are small at 2.5 μM. Such cell morphology indicates apoptosis.

Figure 3A:
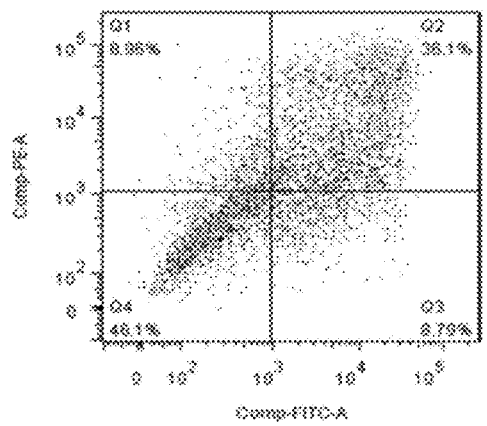
FIG. 3A to 3E show a Flow Cytometry pattern of HCC78 cells having been treated with different concentrations of the compound of Formula (Ic), with crizotinib or of the control group.
Figure 3B:
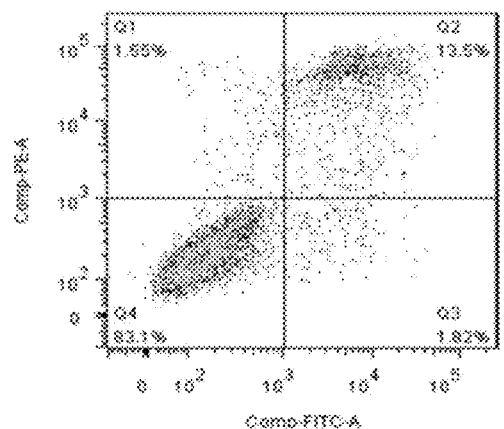
Figure 3C:
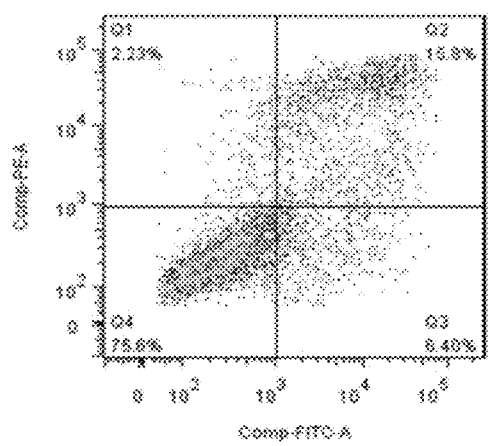
Figure 3D:
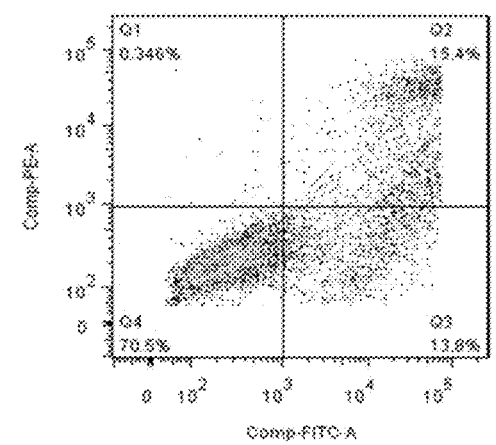
Figure 3E:
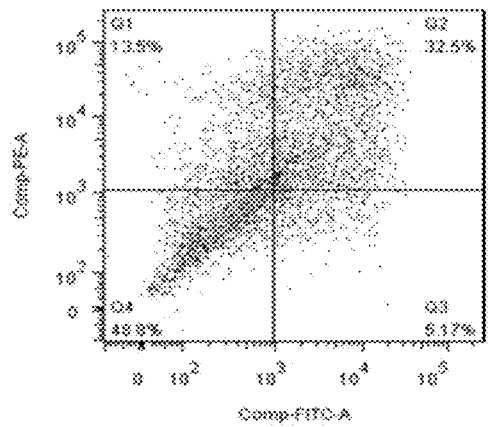
Figure 3F:
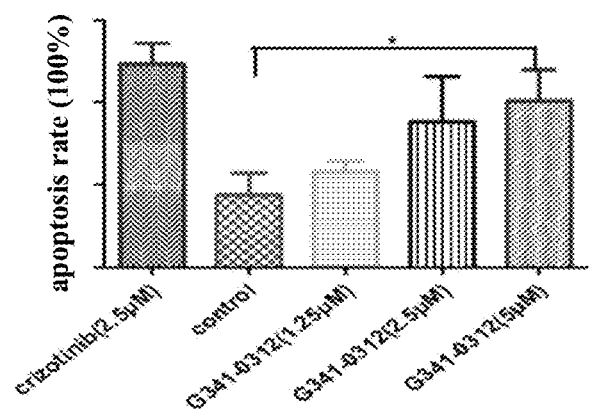
FIG. 3F shows the rate of apoptosis of HCC78 cells having been treated with the compound of Formula (Ic) of the present invention (referenced as "G341-0312") with 1.25 μM, 2.5 μM or 5 μM or 2.5 μM crizotinib compared to the control group.

For a more quantitative view, flow cytometry analysis has been performed. As evident from FIG. 3F, the present compound of Formula (Ic) ("G341-0312") exhibits anti-cancer ability through induction of apoptosis on HCC78 cells in a concentration dependent manner. A significant apoptosis level is observed in HCC78 cells having been treated with the compound of Formula (Ic).

Example 1C

Suppression of ROS1 Phosphorylation and Anti-Apoptotic and Growth Signaling Pathways Downstream to ROS1 by the Compound of Formula (Ic)

The compound of Formula (Ic) also proved to suppress ROS1 phosphorylation and anti-apoptotic and growth signaling pathways that are downstream to ROS1. Previous studies demonstrate that ROS1 fusion kinase signal is activated through the tyrosine phosphatase Src homology-2 domain containing protein tyrosine phosphatase-2 (SHP2) and causes activation of the downstream MEK/ERK, P13K/AKT/mTOR, and JAK/STAT3 signaling axes. Together, these downstream signaling pathways promote tumor cell survival and proliferation. Therefore, inhibition of these downstream signaling pathways suppresses growth and proliferation of cancer cells and results in anti-cancer effect.

The cells were planted on 6-well plate, allowed to attach for 24 h, and treated with the various concentrations of the compound of Formula (Ic) for 72 h. Cells were washed twice with cold PBS then lysed in RIPA lysis buffer containing protease and phosphatase inhibitors. Protein concentration of the cell lysates was measured using the Bio-Rad protein Assay kit (Bio-Rad, 7 Philadelphia, Pa., USA). After equalizing the protein concentrations of the samples, 5× laemmli buffer was added and the samples were boiled at 100° C. for 5 min. Equal amounts of protein samples (30 μg) were subjected to SDS-PAGE of a 10% gel. The separated proteins were transferred to a nitrocellulose (NC) membrane, which was then exposed to 5% non-fat dried milk in TBS containing 0.1% Tween (0.1% TBST) for 1 h at room temperature, followed by overnight incubation at 4° C. with primary antibodies to GAPDH, phospho-AKT, AKT, phospho-ROS1, ROS1, phospho-ERK, ERK, phospho-STAT3, STAT3. After washing three times by TBST (5 mins/time), the membranes were incubated for 1 h at room temperature with the secondary fluorescent antibodies (1:10000 dilutions) to rabbit or mouse. The signal intensity of the membranes was detected by an LI-COR Odessy scanner (Belfast, Me., USA).

Figure 4:
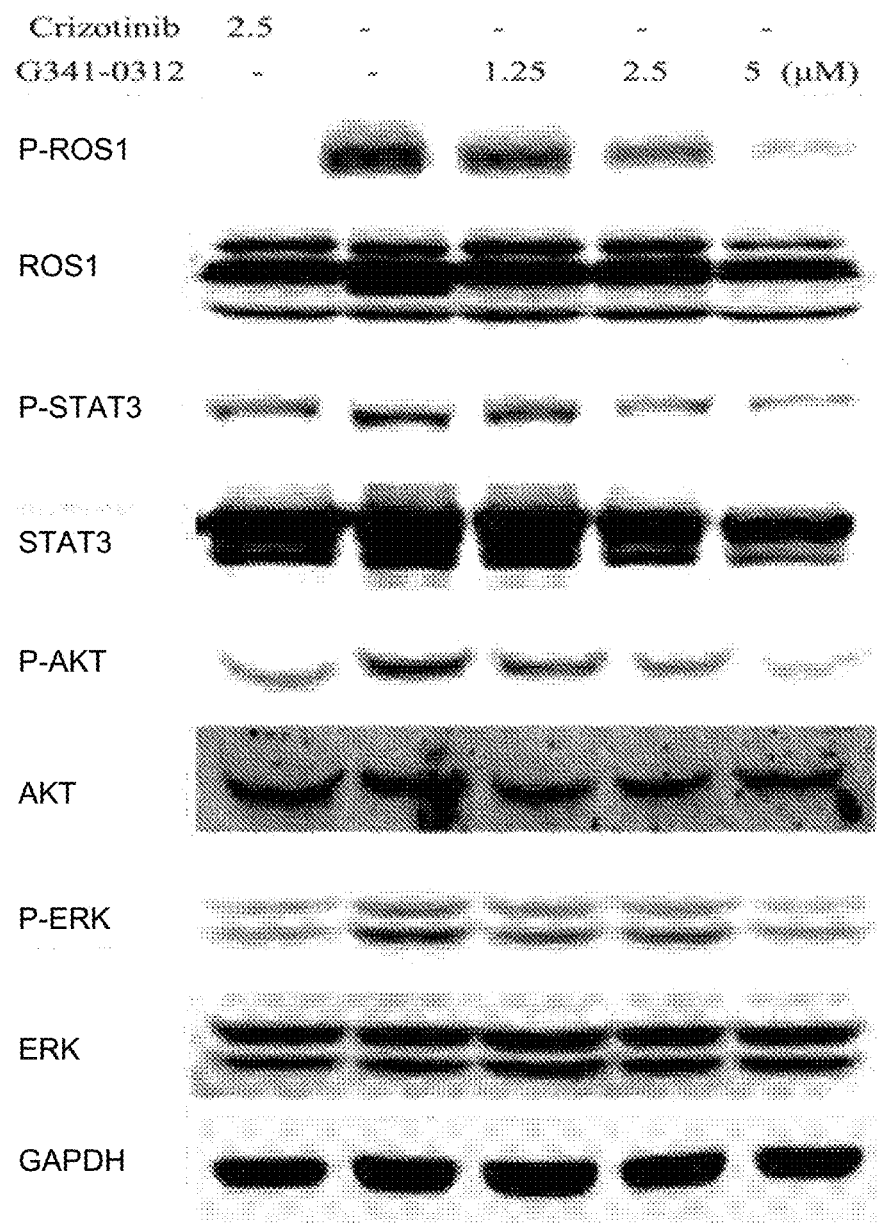
FIG. 4 refers to a western blot and shows the expression of phosphorylated ROS1, ROS1, phosphorylated AKT, AKT, phosphorylated STAT3, STAT3, phosphorylated ERK, ERK and GAPDH of a control group and HCC78 cells treated with 2.5 μM crizotinib, 1.25 μM, 2.5 μM or 5 μM of the compound of Formula (Ic) (referenced as "G341-0312").

Treatment of HCC78 cells with the compound of Formula (Ic) ("G341-0312") led to a dose-dependent decrease of ROS1 phosphorylation as well as of its downstream signaling involving Erk1/2, STAT3 and AKT, further supporting the anti-cancer effect of the compound of Formula (Ic) (FIG. 4). Crizotinib has been used as positive control.

Example 1D

Binding Mode Between the Compound of Formula (Ic) and ROS1 Kinase

The binding mechanism of the compound of Formula (Ic) to ROS1 kinase has been studied. Molecular docking calculation was performed to study the interaction between compound of Formula (Ic) and ROS1 kinase by Induced Fit Docking module in Schrodinger software (Schrodinger, Inc., New York, N.Y., 2009). Compound of Formula (Ic) was prepared and optimized in the LigPrep module.

During the induced fit docking, centroid of the crizotinib was defined as the active site and the pose of ligand was valued with XP docking score. The pose with the highest score was selected for further analysis. The 3D structure of ROS1 was derived from the PDB database (PDB ID: 3ZBF) and prepared using the Protein Preparation Wizard.

Figure 5A:
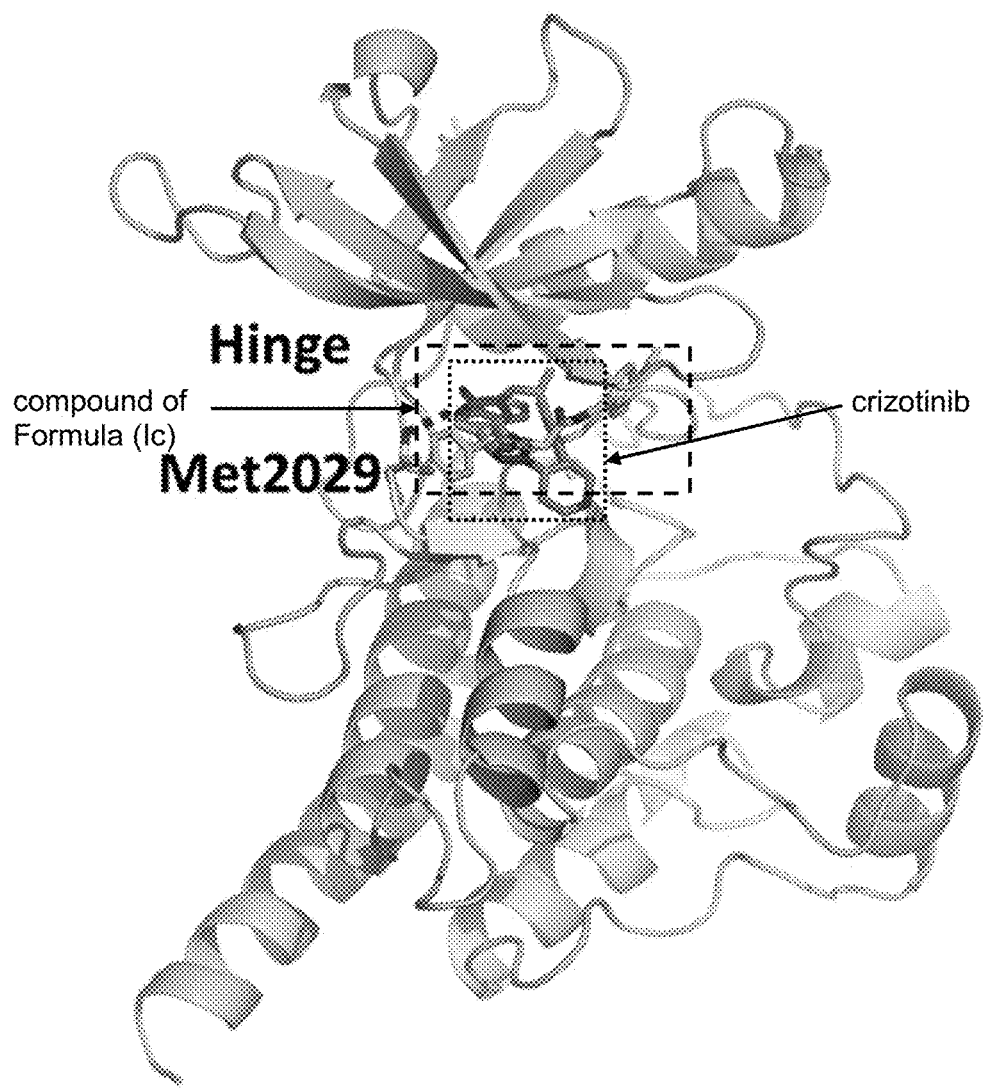
FIG. 5A shows a 3D schematic representation of the compound of Formula (Ic), crizotinib and the binding pocket of the ROS1 kinase domain.
Figure 5B:
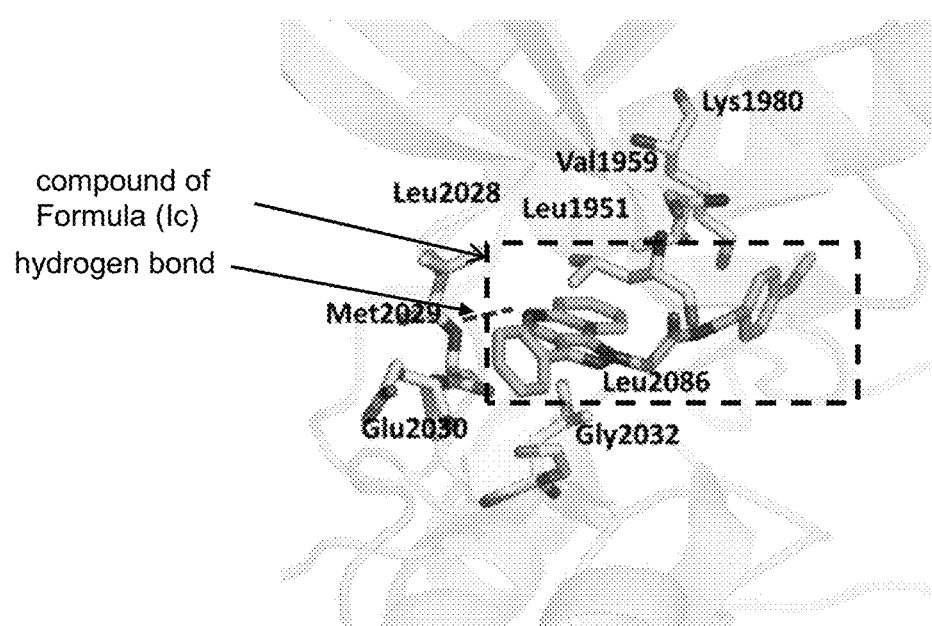
FIG. 5B shows a 3D schematic representation of the binding mode between the compound of Formula (Ic) and the binding pocket of the ROS1 kinase domain.

The compound of Formula (Ic) proved to have a similar binding mechanism to ROS1 kinase domain as crizotinib. The docking scores of the present compound and crizotinib to ROS1 are $-11.157$ and $-9.674$ Kcal/mol, respectively. The present compound is shown to have a better binding affinity to ROS1 than crizotinib. As seen in FIG. 5A, the pyridine groups of both compounds form a hydrogen bond with Met2029 in the hinge region. The phenyl group and the anisole group of the compound of Formula (Ic) allows for extra hydrophobic interactions with the hinge and G-loop, respectively. As shown in FIG. 5B, residues Leu2028, Met2029, Glu2030, Gly2032, Asp2033 in the hinge region have contact with the compound of Formula (Ic), while the residues Leu1951, Val1959 in the G-loop have hydrophobic interactions with the compound of Formula (Ic). Other residues, such as Lys1980, Asp2102, Leu2086, also highly contribute to the binding of the compound of Formula (Ic).

Example 2

Inhibition of ALK Kinase

Further, the efficiency of the compound of Formula (Ic) as inhibitor of ALK kinase has been evaluated including its cytotoxic properties and selectivity towards cancer cells with ALK chromosome rearrangement, its efficacy in inducing cell deaths and inhibition of colony formation in those cells as well as the effects on the ALK phosphorylation and anti-apoptotic and growth signaling pathways downstream to ALK.

Crizotinib was purchased from Selleck Chemicals. G341-0312 was purchased from ChemDiv company. They were dissolved in DMSO to a 50 mM or 20 mM concentration and stored in small aliquots at −20° C. until further use. Antibodies to GAPDH, ALK, p-ALK (1282/1283), p-AKT (Ser473), p-ERK (Thr202/Thy204), ERK were purchased from Cell signaling Technology.

H2228 (which express EML4-ALK fusion kinases, namely variant 3) and BEAS-2B cells were obtained from the American Type Culture Collection and cultured in environment of 5% $CO_2$ at 37° C. in RPMI-1640 medium supplemented with 10% fetal bovine serum (FBS), 100 units/mL penicillin, and 100 μg/mL streptomycin.

Descriptive analytical data were presented as means SEM. Multiple comparisons were evaluated by one-way analysis of variance (ANOVA) followed by using Graph Prim5.0. Values of P<0.05 were considered statistically significant.

Example 2A

Cytotoxic Effects of the Compound of Formula (Ic) Towards Cells with ALK Chromosome Rearrangement The cytotoxicity effect of the compound of Formula (Ic) on H2228 NSCLC cells (harboring ALK fusion) and human bronchial epithelial (BEAS-2B) have been analyzed. H2228 cells were cultured in 96-well plates at a density of $3 \times 10^3$ cells/well, and were cultured overnight for cell adhesion. Then the cells were treated with DMSO or various concentrations of the compound of Formula (Ic) for 72 h. To each well 10 μL MTT (5 mg/mL) (Sigma) was added and the cells were incubated for another 4 h at 37° C., followed by adding 100 μL acidic isopropanol (10% SDS, and 0.01 mol/L HCl). Finally, the optical density (OD) of each well was measured at 570 nm by the Microplate Reader (Epoch, Winooski, USA). The cell viability was calculated relative to untreated controls, with results based on at least three independent experiments.

Figure 6A:
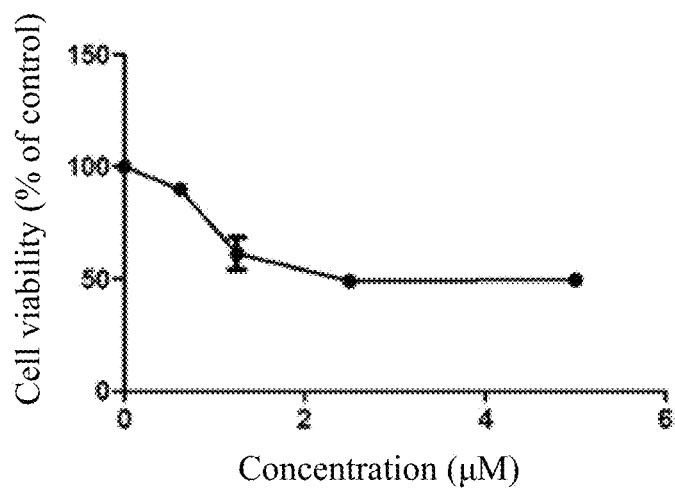
FIG. 6A shows the cell viability of H2228 cells after 72 hours treatment with the compound of Formula (Ic) of the present invention.
Figure 6B:
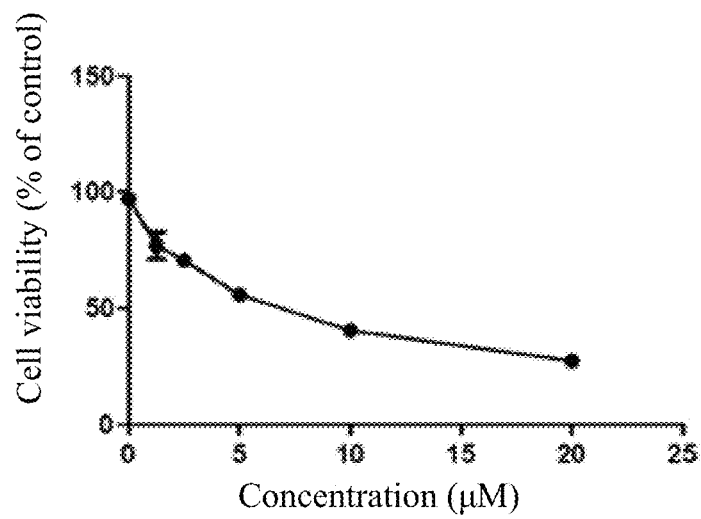
FIG. 6B shows the cell viability of BEAS-2B cells after 72 hours treatment with the compound of Formula (Ic) of the present invention.
Figure 7A:
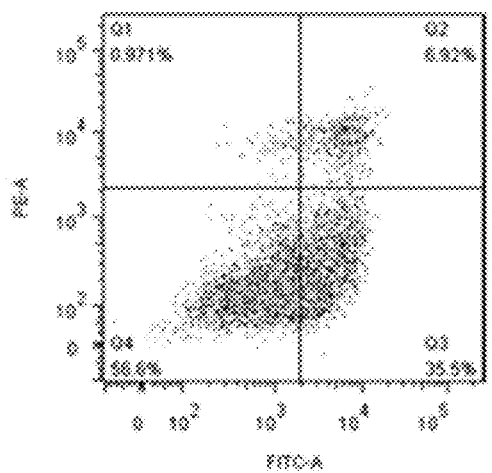
FIG. 7A to 7E show a Flow Cytometry pattern of H2228 cells having been treated with different concentrations of the compound of Formula (Ic) of the present invention, with crizotinib or of the control group.
Figure 7B:
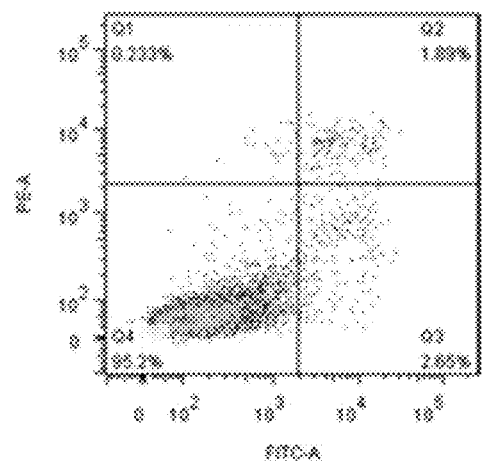
Figure 7C:
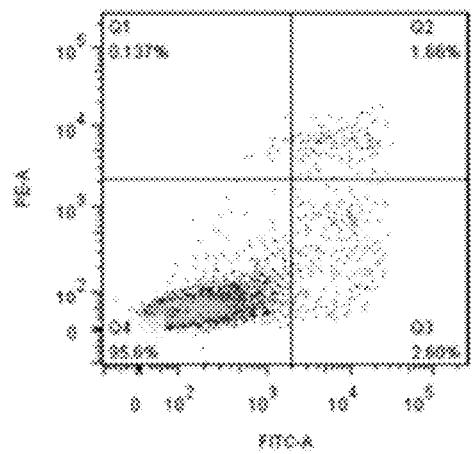
Figure 7D:
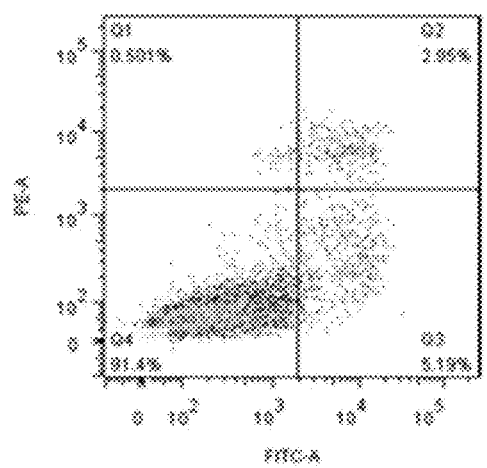
Figure 7E:
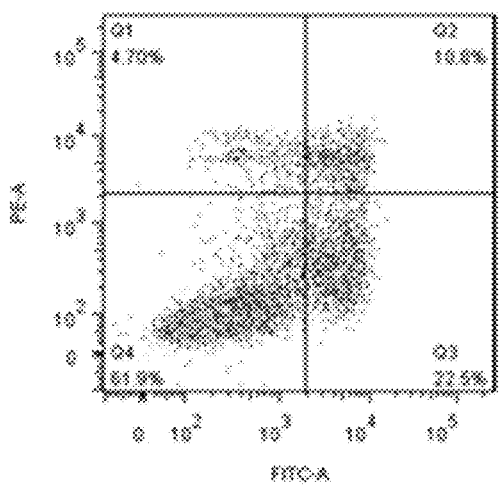
Figure 7F:
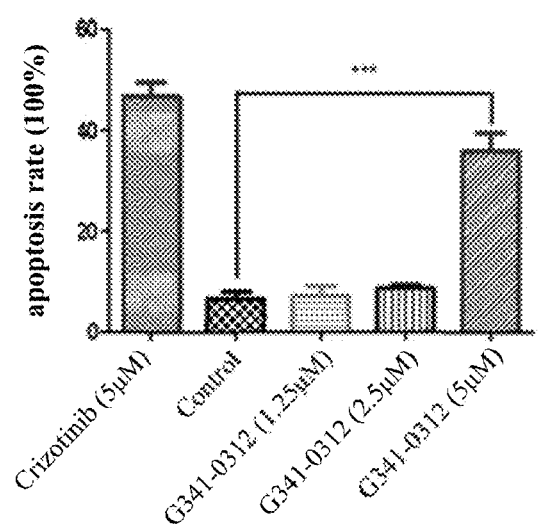
FIG. 7F shows the rate of apoptosis of H2228 cells having treated with the compound of Formula (Ic) of the present invention (referenced as "G341-0312") with 1.25 μM, 2.5 μM or 5 μM or with 5 μM crizotinib compared to the control group.
Figure 8A:
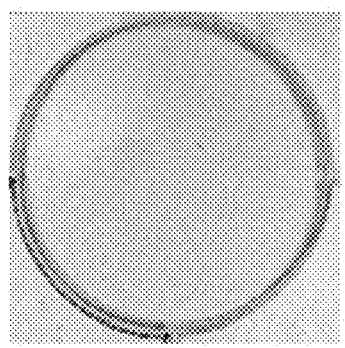
FIG. 8A to 8E show the formation of H2228 cell colonies after treatment with different concentrations of the compound of Formula (Ic), crizotinib or of the control group.
Figure 8B:
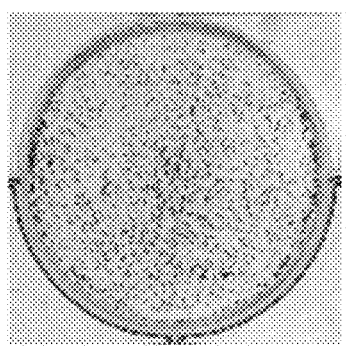
Figure 8C:
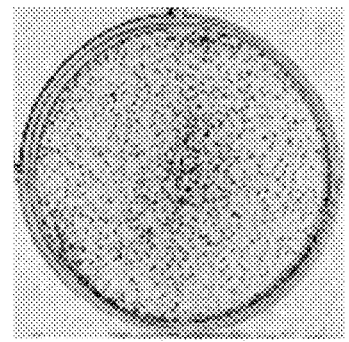
Figure 8D:
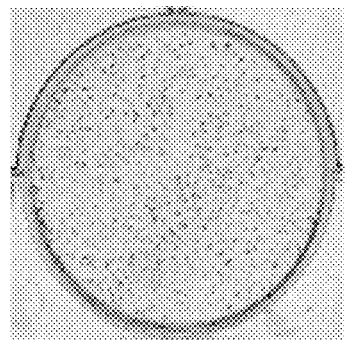
Figure 8E:
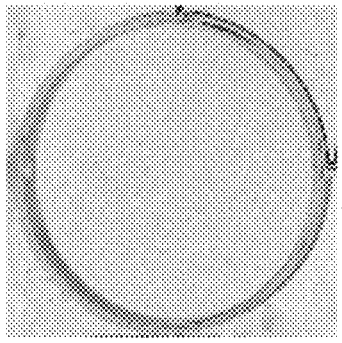
Figure 8F:
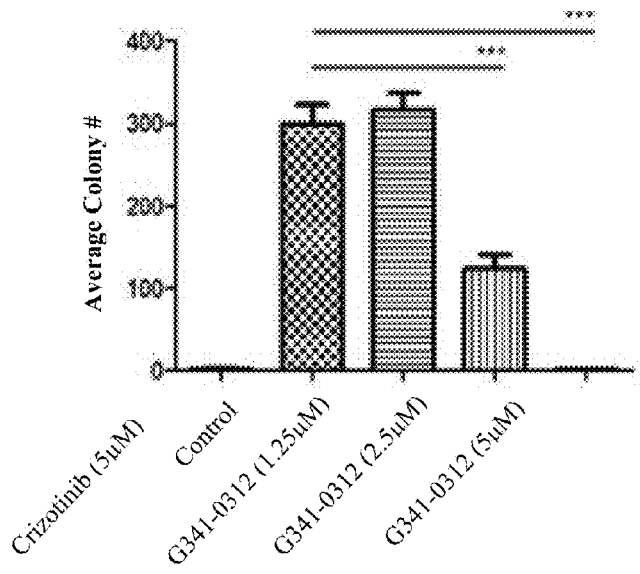
FIG. 8F illustrates the average number of colonies formed in the colony formation assay as shown in FIG. 8A to 8E, i.e. with 1.25 μM, 2.5 μM and 5 μM of the compound of Formula (Ic) (referenced as "G341-0312") compared with 5 μM crizotinib and control group.

MTT assay showed that treatment with the compound of Formula (Ic) was associated with a concentration-dependent significantly decreased cell viability, with an $IC_{50}$ value of 2.71±0.92 μM and lower cytotoxicity on normal lung cells BEAS-2B (see FIGS. 6A and 6B and table 2).

TABLE 2

| $IC_{50}$ of the compound of Formula (Ic) | |
|---|---|
| Cell line | $IC_{50}$ (μM) |
| H2228 | 2.71 ± 0.92 |
| BEAS-2B | 6.51 ± 1.08 |

Example 2B

Induction of Apoptosis in H2228 Cells by the Compound of Formula (Ic)

H2228 cells ($1.0 \times 10^5$ cells/well) were allowed to attach in a 6-well plate for 24 h. The cells were treated with various concentrations of the compound of Formula (Ic), namely 1.25, 2.5 and 5 μM, for 48 h. Subsequently, cells were trypsinized, washed with PBS twice, then the cells were resuspended in a total volume of 100 μL binding buffer with 2 μL Annexin-V FITC and 5 μL propidine iodide (PI). Finally, the cells were gently mixed and incubated in the dark at room temperature for 15 min, before further addition of 400 μL of 1× Annexin-binding buffer, the number of apoptotic cells was quantified using a Flow Cytometer (BD Biosciences, San Jose, Calif., USA) within 1 h. Data were analyzed by Flow Jo software.

Flow cytometry analysis showed that the compound of Formula (Ic) induced cell death through induction of apoptosis of H2228 cells in a concentration-dependent manner (FIG. 7A to FIG. 7F). Compared with the control group, treatment on H2228 cells with the compound of Formula (Ic) induced significant levels of cell apoptosis especially in a concentration of at least 5 μM (FIG. 7A to FIG. 7F).

Example 2C

Suppression of Colony Formation of H2228 Cells by the Compound of Formula (Ic)

H2228 cells were seeded to six-well plate (1000/well). Then cells were exposed to various doses of the compound of Formula (Ic), namely 1.25, 2.5 and 5 μM. After 14 days, colonies were fixed with 4% paraformaldehyde for 15 min and stained with crystal violet for 10-15 min. Finally, the staining solution was slowly washed off with water and the cells were air dried. Clones with more than 50 cells were counted under a microscope.

The colony formation assay revealed that the compound of Formula (Ic) inhibited the formation of H2228 cell colonies in a dose-dependent manner (FIG. 8A to FIG. 8F). Especially when the concentration of the compound of Formula (Ic) reached 5 μM, H2228 cells formed no visible colonies.

Example 2D

Suppression of ALK Phosphorylation and Anti-Apoptotic and Growth Signaling Pathways Downstream to ALK by the Compound of Formula (Ic)

Cells treated with different concentrations of the compound of Formula (Ic) (1.25, 2.5 or 5 μM) or 5 μM of crizotinib or a control group were washed twice with cold PBS then lysed in RIPA lysis buffer containing protease and phosphatase inhibitors, protein concentrations were determined by Bio-Rad protein Assay kit (Bio-Rad, Philadelphia, Pa., USA). after equalizing the protein concentrations of the samples, 5× laemmli buffer was added and boiled at 100° C. for 5 min. Equal amounts of the protein samples (20-40 μg per lane) were separated on a 10% SDS-PAGE gel, then proteins were transferred onto Nitrocellulose (NC) membrane at 300 mA for 2.5 hours at 4° C., the membranes was probed with primary antibodies overnight at 4° C. which was then exposed to 5% non-fat dry milk in TBST for 1 h at room temperature with constant agitation and, then, rabbit or mouse fluorescent antibodies (1:1000) were added to the membrane at room temperature for 1 h. Visualization was performed using a LI-COR Odessy scanner (Belfast, Me., USA). All primary antibodies were diluted 1:1000, while their recommended secondary antibodies were diluted 1:10000.

Figure 9:
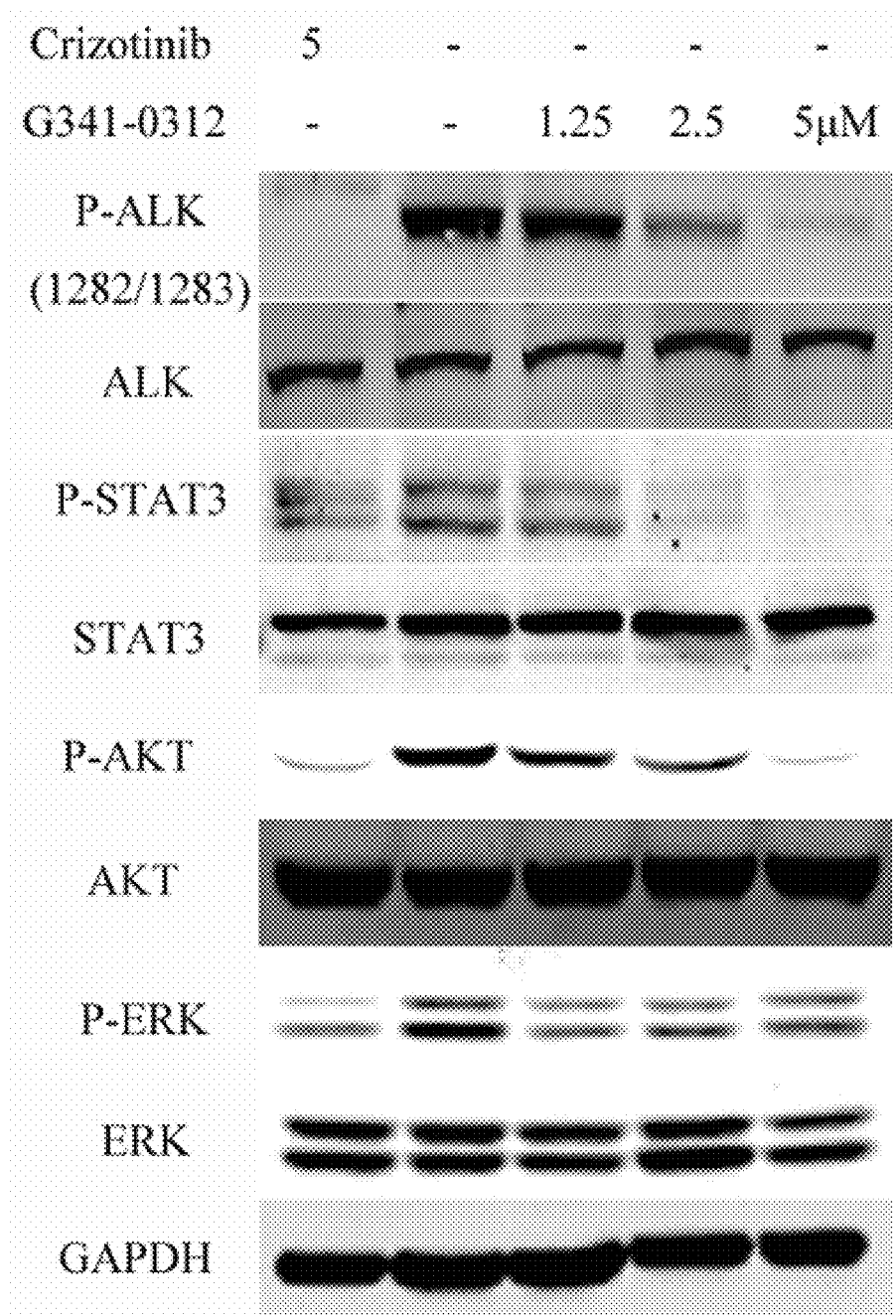
FIG. 9 refers to a western blot and shows the expression of phosphorylated ALK, ALK, phosphorylated AKT, AKT, phosphorylated STAT3, STAT3, phosphorylated ERK, ERK and GAPDH of a control group and H2228 cells treated with 5 μM crizotinib, with 1.25 μM, 2.5 μM or 5 μM of compound of Formula (Ic) (referenced as "G341-0312").

The anti-tumor efficacy of the compound of Formula (Ic) was dose-dependent and led to significant suppression of ALK phosphorylation as well as the downstream PI3K/AKT, MEK/ERK and JAK/STAT3 signaling pathways (FIG. 9).

Example 2E

Binding Mode Between the Compound of Formula (Ic) and ALK Kinase

Molecular docking calculation was performed to study the interaction mode between the compound of Formula (Ic) and the kinase binding domain of ALK by Induced Fit Docking module in Schrodinger software (Schrodinger, Inc., New York, N.Y., 2009). The studied compound of Formula (Ic) was prepared and optimized in the LigPrep module. The 3D structure of ALK was derived from the PDB database (PDB ID: 2XP2) and prepared using the Protein Preparation Wizard. During the induced fit docking calculation, the co-crystalized inhibitor crizotinib was used to define the active site. The poses of the studied compound were evaluated by standard precision (SP) docking score and the conformation with the highest score is selected for binding mode analysis.

Figure 10A:
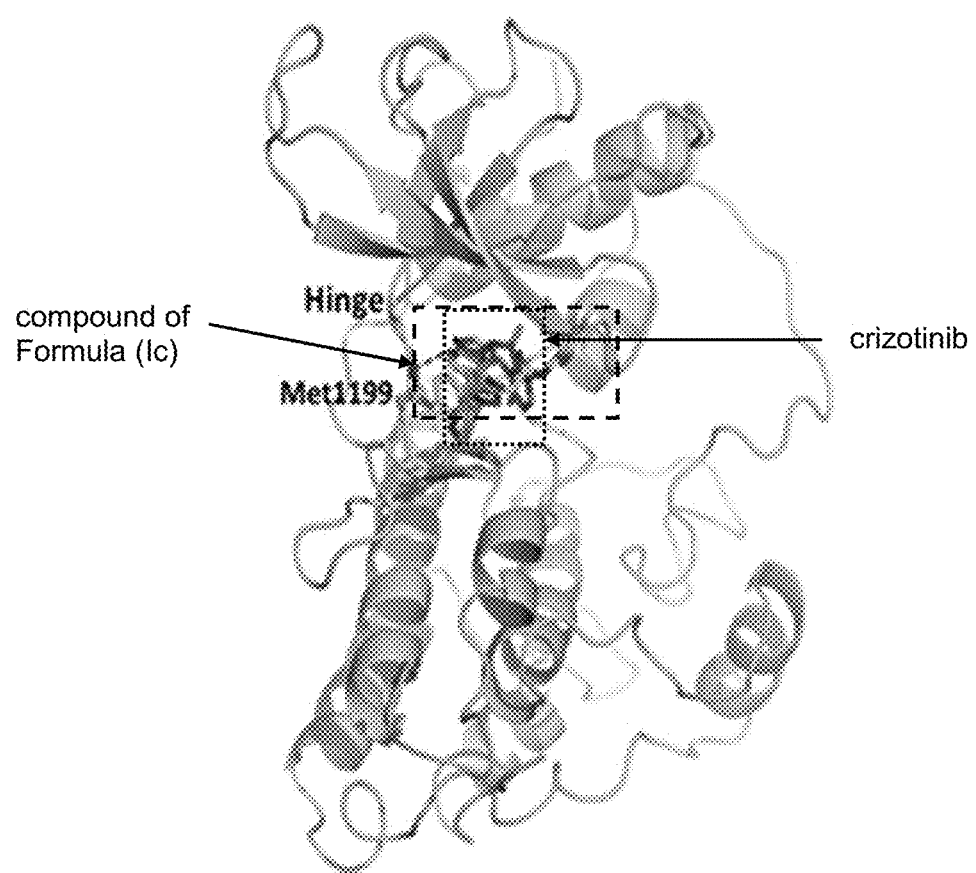
FIG. 10A shows a 3D schematic representation of the compound of Formula (Ic), crizotinib and the binding pocket of the ALK kinase domain.
Figure 10B:
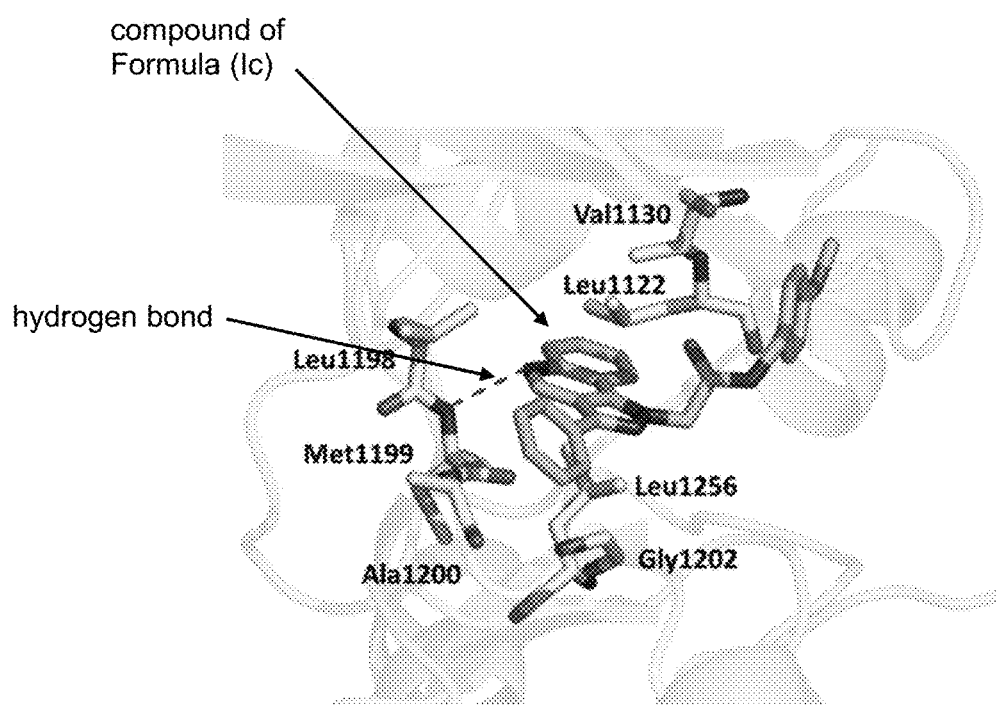
FIG. 10B shows a 3D schematic representation of the binding mode between the compound of Formula (Ic) and the binding pocket of the ALK kinase domain.

The binding affinity of the compound of Formula (Ic) and ALK was evaluated by the SP docking score. The docking score of the compound of Formula (Ic) is −9.413 Kcal/mol. The conformation of the compound of Formula (Ic) has been superimposed with the co-crystalized ligand crizotinib to compare their binding modes. As shown in FIG. 10A, the scaffold of the compound of Formula (Ic) overlapped well with the location of crizotinib, while both molecules formed hydrogen bonds with residue Met1199 in the hinge domain. As shown in FIG. 10B, the compound of Formula (Ic) was buried in a hydrophobic pocket formed by Leu1122, Val1130, Leu1198, Met1199, Ala1200, Gly1202, Leu1256 in the kinase binding domain such as in the catalytic spine.

INDUSTRIAL APPLICABILITY

The present invention provides a new inhibitor, compound of Formula (Ia), in particular of Formula (Ib) or (Ic), that can specific target oncogenic ROS1 kinase and, furthermore, oncogenic ALK kinase, which exhibits potent anti-cancer activity, especially in NSCLC cell with ROS1 fusion gene or ALK fusion gene. The compound of Formula (Ia) is suitable to suppress ROS1 and ALK phosphorylation as well as respective downstream anti-apoptotic and growth signaling effectors, including PI3K/AKT, MEK/ERK and JAK/STAT3 signaling pathways. The present compound shows low toxicity to normal lung epithelial cells, which can, thus, be used as anti-cancer drug for targeting a subgroup of cancer patients who harbor different forms of abnormalities in the ROS1 gene or ALK gene, in particular chromosome rearrangements.

The invention claimed is:

1. A method of treating a subject suffering from non-small cell lung cancer comprising administering an effective amount of a compound of Formula (Ic) or a pharmaceutically acceptable salt, solvate or anhydrate thereof to the subject:

Formula (Ic)

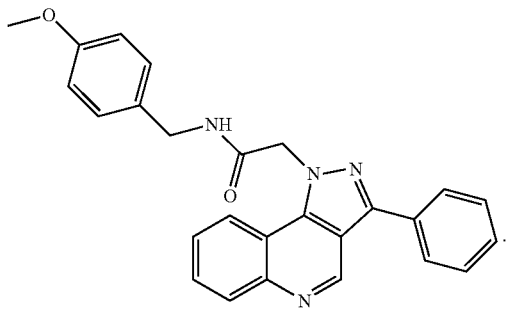

2. A method of Inhibiting ROS1 kinase activity or ALK kinase activity in non-small cell lung cancer cells comprising administering an effective amount of a compound of Formula (Ic) or a pharmaceutically acceptable salt, solvate or anhydrate thereof to a subject suffering from cancer:

Formula (Ic)

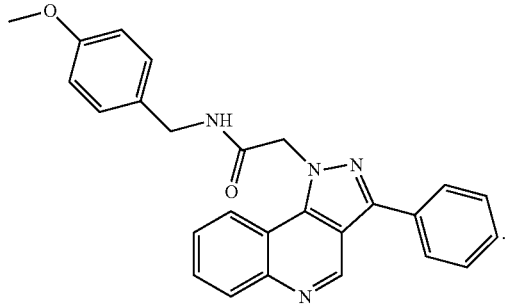

3. The method of claim 1, wherein the subject is a mammal having an abnormality in ROS1 gene resulting from a ROS1 chromosome rearrangement.

4. The method of claim 3, wherein the ROS chromosome rearrangement is associated with the expression of at least one of SLC34A2-ROS1 or CD74-ROS1 fusion kinase.

5. The method of claim 1, wherein the subject is a mammal having an abnormality in ALK gene resulting from an ALK chromosome rearrangement.

6. The method of claim 5, wherein the ALK chromosome rearrangement is associated with the expression of at least one EML4-ALK fusion kinase.

7. A method for targeting non-small cell lung cancer cells harboring an abnormality in ROS1 gene or an abnormality in ALK gene comprising the step of contacting said cells with a compound of Formula (Ic) or a salt, solvate or anhydrate thereof:

Formula (Ic)

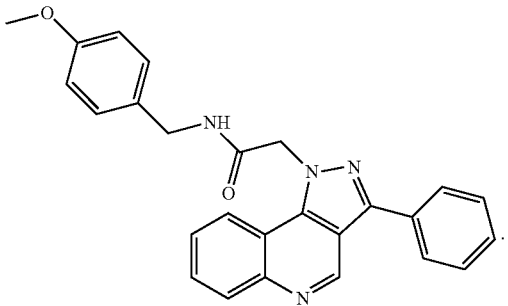

8. The method of claim 7, wherein the proliferation of the non-small cell lung cancer cells is Inhibited, reduced or prevented or apoptosis of the non-small cell lung cancer cells is Induced.

9. The method of claim 7, wherein the non-small cell lung cancer cells are from a lung tumor.

10. The method of claim 7, wherein the non-small cell lung cancer cells are from NSCLC adenocarcinoma.

11. The method of claim 7, wherein the non-small cell lung cancer cells harbor an abnormality in ROS1 gene, and wherein said abnormality is a ROS1 chromosome rearrangement associated with the expression of at least one of SLC34A2-ROS1 or CD74-ROS1 fusion kinase.

12. The method of claim 11, wherein the compound has an $IC_{50}$ on the non-small cell lung cancer cells of at most 10 μM and an $IC_{50}$ on non-cancerous lung cells being at least 2.5 times higher than the $IC_{50}$ on the non-small cell lung cancer cells.

13. The method of claim 7, wherein the non-small cell lung cancer cells harbor an abnormality in ALK gene, and wherein said abnormality is an ALK chromosome rearrangement and wherein the ALK chromosome rearrangement Is associated with the expression of at least one EML4-ALK fusion kinase.

14. The method of claim 13, wherein the compound has an $IC_{50}$ on the non-small cell lung cancer cells of at most 10 μM and an $IC_{50}$ on normal non-cancerous lung cells being at least 2 times higher than the $IC_{50}$ on the non-small cell lung cancer cells.

15. The method of claim 7, wherein the compound of Formula (Ic) is used in a concentration of at least 1.25 μM.

16. The method of claim 7, wherein the concentration of the compound of Formula (Ic) is at least 2.5 μM.

17. The method of claim 7, wherein the non-small cell lung cancer cells are contacted with the compound for at least 12 h.

* * * * *